(12) United States Patent
Band et al.

(10) Patent No.: US 6,867,292 B1
(45) Date of Patent: Mar. 15, 2005

(54) CHARACTERIZATION OF NOVEL GENE CBL-SL

(75) Inventors: Hamid Band, Brookline, MA (US); Francescopaolo Borriello, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/434,708

(22) Filed: Nov. 5, 1999

Related U.S. Application Data
(60) Provisional application No. 60/107,470, filed on Nov. 6, 1998.

(51) Int. Cl.[7] .......................... C07H 23/04; C12P 21/06
(52) U.S. Cl. .................. 536/23.5; 424/278.1; 435/69.1; 435/253.3; 435/320.1
(58) Field of Search .......................... 435/252.3, 320.1, 435/69.1; 424/278.1; 536/23.5

(56) References Cited

PUBLICATIONS

Ngo et al, In Protein Folding & Tertiary Structure Prediction Merz ed. pp. 491–495, 1994.*
Mikayama et al P.N.A.S. 90:10056–10060.*
Voet. Biochemistry p. 126–128 & 228–234, 1990.*
Erdreich–Epstein A et al., "Cbl Functions Downstream of Src Kinases in Fc Gamma RI Signaling in Primary Human Macrophages," *J. Leukoc. Biol.* 1999, 65(4):523–34—Abstract Only.
Ettenberg SA et al., "cbl–b Inhibits Epidermal Growth Factor Receptor Signaling," *Oncogene* 1999 18(10):1855–66—Abstract Only.
Levkowitz G et al., "c–Cbl/Sli–1 Regulates Endocytic Sorting and Ubiquitination of the Epidermal Growth Factor Receptor," *Genes Dev.*, 1998, 12(23):3663–74—Abstract Only.
McCarty JH et al., "The TrkB Receptor Tyrosine Kinase Regulates Cellular Proliferation Via Signal Transduction Pathways Involving SHC, PLCgamma, and CBL," *J. Recept. Signal Transduct. Res.* 1999, 19(6):953–74—Abstract Only.
Yokouchi, Masahiro et al., "Ligand–Induced Ubiquitination of the Epidermal Growth Factor Receptor Involves The Interaction of the c–Cbl RING Finger and UbcH7," *The Journal of Biological Chemistry*, vol. 274, No. 44, 1999, pp. 31707–31712.

Joazeiro CA et al., "The Tyrosine Kinase Negative Regulator c–Cbl as a RING–Type, E2–Dependent Ubiquitin–Protein Ligase," *Science* 1999, 286(5438):309–12—Abstract Only.
van Leeuwen JE et al., "The Oncogenic 70Z cbl Mutation Blocks the Phosphotyrosine Binding Domain–Dependent Negative Regulation of ZAP–70 by c–Cbl in Jurkat T Cells," *Mol. Cell. Biol.* 1999, 19(10):6652–64—Abstract Only.
Waterman H et al., "The RING Finger of c–Cbl Mediates Desensitization of the Epidermal Growth Factor Receptor," *The Journal of Biological Chemistry*, 1999, vol. 274, No. 32, pp. 22151–22154.
Lupher ML, et al., "The Cbl Protooncoprotein: A Negative Regulator of Immune Receptor Signal Transduction," *Immunology Today*, 1999, vol. 20, No. 8, pp. 375–382.
Lee PS et al., "The Cbl Protooncoprotein Stimulates CSF–1 Receptor Multiubiquitination and Endocytosis, And Attenuates Macrophage Proliferation," *EMBO J.* 1999 18(13):3616–28—Abstract Only.
Feshchenko EA et al., "Tyrosine Phosphorylation of C–Cbl Facilitates Adhesion and Spreading While Suppressing Anchorage–Independent Growth of V–Abl–Transformed NIH3T3 Fibroblasts," *Oncogene*, 1999, 18(25):3703–15—Abstract Only.
Keane MM et al., "cbl–3:A New Mammalian cbl Family Protein," *Oncogene* 1999, 18(22):3365–75 Abstract Only.
Broome MA et al., "The Proto–Oncogene c–Cbl is a Negative Regulator of DNA Synthesis Initiated by Both Receptor and Cytoplasmic Tyrosine Kinases," *Oncogene* 1999, 18(18):2908–12—Abstract Only.
Thien CB et al., "Perturbed Regulation of ZAP–70 and Sustained Tyrosine Phosphorylation of LAT and SLP–76 in c–Cbl–Deficient Thymocytes," *J. Immunol.* 1999, 162(12):7133–9—Abstract Only.
Miyake S et al., "Cbl–Mediated Negative Regulation of Platelet–Derived Growth Factor Receptor–Dependent Cell Proliferation," *The Journal of Biological Chemistry*, 1999, vol. 274, No. 23, pp. 16619–16628.

* cited by examiner

*Primary Examiner*—G. R. Ewoldt
(74) *Attorney, Agent, or Firm*—Wolf, Greenfield & Sacks, PC

(57) ABSTRACT

The invention pertains to nucleic acids encoding a cbl-SL protein, including fragments and biologically functional variants thereof. The invention also pertains to therapeutics and diagnostics involving the foregoing proteins and genes and agents that bind the foregoing proteins and genes.

6 Claims, 9 Drawing Sheets

CHARACTERIZATION OF NOVEL GENE CBL-SL

RELATED APPLICATIONS

This application claims priority under 35 U.S.C. §119 from Provisional U.S. Patent Application Ser. No. 60/107,470 filed on Nov. 6, 1998, entitled CHARACTERIZATION OF NOVEL GENE CBL-SL. The contents of the provisional application are hereby expressly incorporated by reference.

GOVERNMENT SUPPORT

This work was funded in part by grant numbers RO1-CA75075-02 and RO1-CA76118-01 from the National Institutes of Health, and IM-79014 from the American Cancer Society. Accordingly, the United States Government may have certain rights to this invention.

FIELD OF THE INVENTION

This invention relates to nucleic acids and encoded polypeptides of cbl-SL, and diagnostics and therapeutics related to medical conditions associated with such genes and polypeptides, including cancers.

BACKGROUND OF THE INVENTION

Tyrosine phosphorylation provides a universal mechanism of signal transduction in response to extracellular cues that regulate proliferation and differentiation in normal cells. Uncontrolled tyrosine kinase activation is implicated in proliferation of cancerous cells and deficiencies of specific tyrosine kinases result in a number of pathological conditions such as developmental abnormalities or immunodeficiencies. Little is known at present about how cellular tyrosine kinases are regulated. Genetic studies in C. elegans have identified the sli-1 proto-oncogene product as a potential regulator of tyrosine kinase signaling.

Sli-1 is a member of the Cbl family of proto-oncogenes that includes c-Cbl, Cbl-b and the Drosophila gene D-Cbl. Recent studies report that Cbl, the 120 kDa protein product of the c-cbl proto-oncogene (first identified as part of a transforming gene of a murine retrovirus and whose expression is predominant in haematopoietic cells), consists of an amino-terminal transforming region, a zinc ring finger, multiple proline-rich stretches, and several potential phosphotyrosine-containing motifs.

Cbl is reportedly tyrosine-phosphorylated, at a fast rate, in response to stimulation of a variety of cell-surface receptors and upon integrin-mediated cell adhesion. Cbl becomes associated with a number of intracellular signalling molecules such as protein tyrosine kinases, phosphatidylinositol-3-kinase, Crk, 14-3-3 proteins, and other cytoskeletal and adaptor proteins through different protein-interacting modules (including Src Homology 2 and 3-i.e., SH2 and SH3-domains), leading to the formation of multimolecular signalling complexes. Cbl can be rendered into a transforming factor by engineering mutations into its amino acid sequence. Cbl and its transforming mutants have been reported to display both negative and positive regulatory activities in protein tyrosine kinase- and Ras-mediated signalling pathways. The N-terminal region of c-Cbl (c-Cbl-N) harbors a tyrosine kinase binding domain, which presumably plays a regulating role in c-Cbl's transforming capabilities.

There exists a need to identify agents that desirably influence a cell's growth, differentiating and proliferative characteristics, and to provide diagnostics, research tools and therapeutics relating to such novel agents.

These and other objects will be described in greater detail below.

SUMMARY OF THE INVENTION

We describe herein the molecular cloning and characterization of cbl-SL, a novel molecule that is believed to play a role in the regulation of a cell's growth, differentiation and proliferation. Aberrant expression levels and mutant forms of tyrosine kinases which are the likely targets of cbl-SL have been found in patients with certain types of cancer, suggesting that cbl-SL may play a role in cell cycle control and cancerous cell proliferation in particular.

The invention provides isolated nucleic acid molecules, unique fragments of those molecules, expression vectors containing the foregoing, and host cells transfected with those molecules. The invention also provides isolated binding polypeptides and binding agents which bind such polypeptides, including antibodies. The foregoing can be used, inter alia, in the diagnosis or treatment of conditions characterized by the aberrant expression levels and/or the presence of mutant forms of a cbl-SL nucleic acid or polypeptide. The invention also provides methods for identifying pharmacological agents useful in the diagnosis or treatment of such conditions.

According to one aspect of the invention, isolated nucleic acid molecules that code for a cbl-SL polypeptide are provided and include: (a) nucleic acid molecules which hybridize under stringent conditions to a molecule consisting of a nucleic acid of SEQ ID NO: 1 and which code for a cbl-SL polypeptide, (b) deletions, additions and substitutions of (a) which code for a respective cbl-SL polypeptide, (c) nucleic acid molecules that differ from the nucleic acid molecules of (a) or (b) in codon sequence due to the degeneracy of the genetic code, or (d) complements of (a), (b) or (c). In certain embodiments, the isolated nucleic acid molecule comprises nucleotides 1–1547 of SEQ ID NO:1. In some embodiments the isolated nucleic acid molecules are those comprising the human cDNA or gene corresponding to SEQ ID NO:3. The isolated nucleic acid molecule also can comprise a molecule which encodes the polypeptide of SEQ ID NO:2 and has cbl-SL binding activity.

The invention in another aspect provides an isolated nucleic acid molecule selected from the group consisting of (a) a unique fragment of nucleic acid molecule of SEQ ID NO:1 (of sufficient length to represent a sequence unique within the human genome), (b) complements of (a), provided that the fragment includes a sequence of contiguous nucleotides which is not identical to a sequence selected from the sequence group consisting of (1) sequences having the GenBank and EMBL accession numbers of Table 1, (2) complements of to (1), and (3) fragments of (1) and (2).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In another embodiment, the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect, the invention provides expression vectors, and host cells transformed or transfected with such expression vectors, comprising the nucleic acid molecules described above.

According to another aspect of the invention, an isolated polypeptide is provided. The isolated polypeptide is encoded by the foregoing isolated nucleic acid molecules of the invention. In some embodiments, the isolated polypeptide is encoded by the nucleic acid of SEQ ID NO:1, giving rise to a ~50 kd polypeptide having the sequence of SEQ ID NO:2 that can associate with a tyrosine kinase to form a complex, and thereby could regulate a cell's growth, differentiation and proliferation. In other embodiments, the isolated polypeptide may be a fragment or variant of the foregoing of sufficient length to represent a sequence unique within the human genome, and identifying with a polypeptide that can associate with a tyrosine kinase to form a complex, and regulate a cell's growth, differentiation and proliferation, provided that the fragment includes a sequence of contiguous amino acids which is not identical to any sequence encoded for by the nucleic acid sequence selected from the group consisting of SEQ ID NO:4, SEQ ID NO:5, SEQ ID NO:6, SEQ ID NO:7, SEQ ID NO:8, and SEQ ID NO:9. In another embodiment, immunogenic fragments of the polypeptide molecules described above are provided.

According to another aspect of the invention, isolated binding polypeptides are provided which selectively bind a polypeptide encoded by the foregoing isolated nucleic acid molecules of the invention. Preferably the isolated binding polypeptides selectively bind a polypeptide which comprises the sequence of SEQ ID NO:2, SEQ ID NO:10, or fragments 10 thereof, and that do not recognize ("cross-react") with epitopes from polypeptides encoded for by the nucleic acid sequence selected from the group consisting of SEQ ID NO:4, SEQ ID NO:5, SEQ ID NO:6, SEQ ID NO:7, SEQ ID NO:8, and SEQ ID NO:9. In preferred embodiments, the isolated binding polypeptides include antibodies and fragments of antibodies (e.g., Fab, F(ab)$_2$, Fd and antibody fragments which include a CDR3 region which binds selectively to the cbl-SL polypeptide). In certain embodiments, the antibodies are human.

The invention also contemplates kits comprising a package including assays for cbl-SL epitopes, cbl-SL nucleic acids, and instructions, and optionally related materials such as controls, for example, a number, color chart, or an epitope of the expression product of the foregoing isolated nucleic acid molecules of the invention, for comparing the level of cbl-SL polypeptides or cbl-SL nucleic acid forms (wild-type or mutant) in a test sample to the level in a control sample. This comparison can be used to assess in a subject a risk of developing a cancer. The kits may also include assays for other known genes, and expression products thereof, associated with cancers (e.g., BRCA, p53, etc.).

According to another aspect of the invention, a method of screening for the presence of a carcinoma in a subject suspected of having a carcinoma is provided. The method involves (a) characterizing cbl-SL nucleic acid sequences in a test sample, wherein the test sample is obtained from a tissue of the subject, and (b) comparing the cbl-SL nucleic acid sequences of the test sample to cbl-SL nucleic acid sequences of a control sample (wild-type or mutant). An observed alteration or match in a cbl-SL nucleic acid sequence in the test sample as compared to cbl-SL nucleic acid sequences in the control sample, is indicative of the presence of carcinoma in the subject. In certain embodiments, the observed alteration is apparent when a cbl-SL nucleic acid sequence in the test sample is compared to wild-type cbl-SL nucleic acid sequences in the control sample. In other embodiments, the observed match is apparent when a cbl-SL nucleic acid sequence in the test sample is compared to mutant cbl-SL nucleic acid sequences in the control sample.

In yet other embodiments, cbl-SL mRNA molecules are compared. Alteration of cbl-SL mRNA may be detected by hybridization of test sample mRNA to any of the foregoing cbl-SL nucleic acids of the invention.

In other embodiments, cbl-SL cDNA sequences are compared. The comparison is performed by hybridization of a cbl-SL cDNA probe to genomic DNA isolated from the test sample. In further embodiments, the genomic DNA is isolated from a non-neoplastic tissue of the subject and is subjected to Southern hybridization with a cbl-SL cDNA probe. The hybridizations are compared to (i) the cbl-SL cDNA probe to the test sample and/or (ii) the cbl-SL cDNA probe to the non-neoplastic tissues. The cbl-SL cDNA probe may detect a restriction fragment length polymorphism.

In yet other embodiments, cbl-SL nucleic acid sequences are compared, and the comparing is performed by determining the sequence of all or part of a cbl-SL cDNA in the test sample using a polymerase chain reaction. Deviations in the cbl-SL cDNA determined from that of the wild-type cbl-SL nucleic acid sequence shown in SEQ ID NO: 1, is indicative of the presence of the carcinoma in the subject.

In certain embodiments, the alteration of cbl-SL nucleic acid sequences is detected by identifying a mismatch between molecules (a) a cbl-SL cDNA or cbl-SL mRNA isolated from the tissue and (b) a nucleic acid probe complementary to the human wild-type cbl-SL nucleic acid sequence, when molecules (a) and (b) are hybridized to each other to form a duplex.

In certain other embodiments, cbl-SL nucleic acid sequences are compared and the alteration of cbl-SL nucleic acid sequences is detected by (a) amplifying cbl-SL cDNA sequences in the test sample, and (b) hybridizing the amplified cbl-SL cDNA sequences to nucleic acid probes which comprise cbl-SL sequences.

In yet other embodiments, cbl-SL nucleic acid sequences are compared, and the alteration of cbl-SL nucleic acid sequences is detected by molecular cloning of cbl-SL sequences in the test sample and characterized by sequencing all or part of the cloned cbl-SL gene.

In any of the foregoing embodiments, detection of alteration of cbl-SL nucleic acid sequences includes screening for a deletion mutation, a point mutation, and/or an insertion mutation. In preferred embodiments, the test sample may be obtained from tissues of a subject that include blood, breast, colon and prostate.

Another aspect of the invention is a method for determining the level of cbl-SL expression in a subject. Expression is defined either as cbl-SL mRNA expression or cbl-SL polypeptide expression. Various methods can be used to measure expression. Preferred embodiments of the invention include PCR and Northern blotting for measuring mRNA expression, and monoclonal or polyclonal cbl-SL antisera as reagents to measure cbl-SL polypeptide expression. In certain embodiments, test samples such as biopsy samples, and biological fluids such as blood, are used as test samples.

Cbl-SL expression in a test sample of a subject is compared to cbl-SL expression in control sample to, e.g., assesss the presence or absence or stage of a cancer in a subject.

The invention in another aspect involves a method for increasing cbl-SL expression in a subject that expresses a mutant cbl-SL. An isolated cbl-SL nucleic acid molecule of the invention or an expression product thereof is administered to a subject expressing a mutant cbl-SL, in an amount effective to increase wild-type cbl-SL expression in the subject.

Another aspect of the invention provides compositions comprising any of the foregoing isolated nucleic acid molecules of the invention, or expression products thereof, and which increase expression of cbl-SL (wild-type), and a pharmaceutically acceptable carrier.

According to another aspect, a method for downregulating (or inhibiting) expression of a tyrosine kinase in a cell is provided. The method involves contacting a cell expressing a tyrosine kinase with a cbl-SL polypeptide, in an amount effective to downregulate expression of the tyrosine kinase in the cell. Preferred cbl-SL polypeptides include the polypeptides of claim 12. In certain embodiments, the tyrosine kinase is selected from the group consisting of a receptor tyrosine kinase, a non-receptor tyrosine kinase, and any of the foregoing tyrosine kinases in complex with another agent. In one embodiment, the tyrosine kinase is ligand activated. In any of the foregoing embodiments, the tyrosine kinase can be phosphorylated. In certain embodiments, the cbl-SL and tyrosine kinase further complexes with an intermediate adapter molecule (e.g., Grb-2).

According to still another aspect of the invention, a method is provided for identifying lead compounds for an agent useful in the diagnosis or treatment of disease associated with cbl-SL activity. The method involves forming a mixture of a cbl-SL polypeptide, a tyrosine kinase that binds a cbl-SL polypeptide (such as the EGF receptor in the presence or absence of other molecules, e.g. Grb-2), and a candidate agent. The mixture is incubated under conditions which permit specific binding of the tyrosine kinase that binds a cbl-SL polypeptide to a cbl-SL polypeptide (i.e., in the absence of a candidate agent). A reference specific binding of the tyrosine kinase that binds a cbl-SL polypeptide to a cbl-SL polypeptide is then detected, the reference specific binding being indicative of cbl-SL activity. The reference specific binding is then compared to a control. Detection of an increase in the foregoing activity relative to the reference specific binding in the presence of the candidate agent indicates that the candidate agent is a lead compound for an agent which increases the cbl-SL activity. Detection of a decrease in the foregoing activities relative to the reference specific binding in the presence of the candidate agent indicates that the candidate agent is a lead compound for an agent which decreases cbl-SL activity. In some embodiments, the binding can occur intracellularly and in a single cell. Preferred cbl-SL polypeptides include the polypeptides of claim 12. In certain embodiments, the tyrosine kinase is selected from the group consisting of a receptor tyrosine kinase, a non-receptor tyrosine kinase, and any of the foregoing tyrosine kinases in complex with another agent. In one embodiment, the tyrosine kinase is ligand activated. In any of the foregoing embodiments, the tyrosine kinase can be phosphorylated. In certain embodiments, the cbl-SL and tyrosine kinase further complexes with an intermediate adapter molecule (e.g., Grb-2).

The present invention thus involves, in several aspects, cbl-SL polypeptides, nucleic acids encoding those polypeptides, functional modifications and variants of the foregoing, useful fragments of the foregoing, as well as therapeutics and diagnostics relating thereto.

These and other aspects of the invention, as well as various advantages and utilities, will be more apparent with reference to the detailed description of the preferred embodiments.

BRIEF DESCRIPTION OF THE SEQUENCES

Figure 1A:
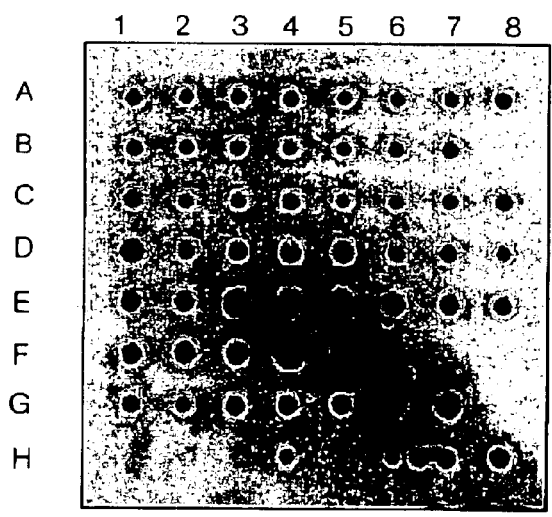
FIG. 1 shows side-by-side comparison of cbl (FIG. 1A) and cbl-SL (FIG. 1B) mRNA expression on identical Tissue Blots.

SEQ ID NO:1 is the nucleotide sequence of the human cbl-SL cDNA.

SEQ ID NO:2 is the predicted amino acid sequence of the translation product of human cbl-SL cDNA (SEQ ID NO:1).

SEQ ID NO:3 is the nucleotide sequence of the largest open reading frame of the human cbl-SL cDNA of SEQ ID NO: 1, encoding for the polypeptide of SEQ ID NO:2.

SEQ ID NO:4 is the nucleotide sequence of a human EST with GenBank Acc. no.: AA 113289.

SEQ ID NO:5 is the nucleotide sequence of a human EST with GenBank Acc. no.: AA112513.

SEQ ID NO:6 is the nucleotide sequence of a sus scrofa cDNA with EMBL Acc. no.: F22931.

SEQ ID NO:7 is the nucleotide sequence of *C. Elegans* sli-1 cDNA with GenBank Acc. no.: X89223.

SEQ ID NO:8 is the nucleotide sequence of human c-cbl cDNA with GenBank Acc. no.: X57110.

SEQ ID NO:9 is the nucleotide sequence of human cbl-b cDNA with GenBank Acc. no.: U26710.

SEQ ID NO:10 is the amino acid sequence of the cbl-SL peptide (aa 445–461 of SEQ ID NO:2) recognized by one of the anti-cbl-SL specific antibodies of the invention.

DETAILED DESCRIPTION OF THE INVENTION

One aspect of the invention involves the cloning of a cDNA encoding cbl-SL. Cbl-SL according to the invention is an isolated nucleic acid molecule that comprises a nucleic acid molecule of SEQ ID NO: 1, and codes for a ~50 kd protein that is believed to play a role in the regulation of a cell's growth, differentiation and proliferation. The sequence of the human cbl-SL cDNA is presented as SEQ ID NO: 1, and the predicted amino acid sequence of this cDNA's encoded protein product is presented as SEQ ID NO:2. Cbl-SL associated functions are believed to be mediated by cbl-SL's binding to other molecules and polypeptides. "Cbl-SL activity," as used herein, refers to the specific binding of cbl-SL to a tyrosine kinase. "Tyrosine kinases" include receptor tyrosine kinases and non-receptor tyrosine kinases. Receptor tyrosine kinases include, but are not limited to, EGRF, PDGFR, CSF-1R (c-fms), c-kit, LET-23R, HGFR/SFR (c-met), FGFR, HER2/neu, HER3, HER4, IGF1R, flt3/flk2, flk1, erbB, c-ret, EphA2, TrkB (BDNFR), tek/tie2, stk, flt-1 (VEGFR), RON, TrkA (NGFR), MuSK, VEGFR2, ROR, tie1, etc. Non-receptor tyrosine kinases include, but are not limited to, Fyn, Lck, Lyn, Syk/ZAP-70, Src, Yes, Hck, Blk, Yrk, Fgr, Rak, Brk, Csk. Tyrosine kinases may be phosphorylated or non-phosphorylated, and receptor tyrosine kinases may be ligand-activated or not activated. Preferably, Cbl-SL binds phosphorylated tyrosine kinases and ligand-activated receptor tyrosine kinases. Cbl-SL activity therefore includes cbl-SL binding at least to the intact Epidermal Growth Factor (EGF) receptor with or without EGF stimulation, or to the Grb-2 (adapter protein) SH2 domain only after EGF stimulation. More preferably, Cbl-SL binds phosphorylated tyrosine kinases and decreases the level of phosphorylation of the tyrosine kinase, and/or dowregulates (or inhibits) expression of the tyrosine kinase.

As used herein, "downregulating expression" refers to inhibiting (i.e., reducing to a detectable extent) replication, transcription, and/or translation of a tyrosine kinase, since inhibition of any of these processes results in the inhibition of expression of the tyrosine kinase polypeptide encoded by the gene. The term also refers to inhibition of post-translational modifications on the tyrosine kinase polypeptide (e.g., in its phosphorylation), since inhibition of such modifications will also prevent proper expression (i.e., expression as in a wild type cell) of the encoded polypeptide. The term also refers to an increase in, or facilitation of, tyrosine kinase degradation (e.g., via increased ubiquitinization). Tyrosine kinase turnover can be determined using methods well known in the art and elsewhere herein (see under the Examples section). The inhibition of gene expression can be directly determined by detecting a decrease in the level of mRNA for the gene, or the level of protein expression of the gene, using any suitable means known to the art, such as nucleic acid hybridization or antibody detection methods, respectively. Inhibition of gene expression can also be determined indirectly by detecting a change in tyrosine kinase activity as a whole (e.g., control of cell cycle, induction of cell growth and/or proliferation, control of cell differentiation, control of cell migration, phosphorylation of target polypeptides, etc.).

In contrast to cbl (and cbl-b), cbl-SL does not bind to N-terminal SH3 domains of the adapter protein Nck (adapter proteins function by mediating the rapid and specific assembly of multi-protein complexes during the signal transduction), and thus, cbl-SL activity excludes such binding.

As used herein, a subject is a human, non-human primate, cow, horse, pig, sheep, goat, dog, cat or rodent. In all embodiments human cbl-SL and human subjects are preferred.

Analysis of the sequence by comparison to nucleic acid and protein databases show that cbl-SL shares a limited homology (58% at the amino acid level) to c-cbl (SEQ ID NO:8) and cbl-b (SEQ ID NO:9). Limited homology is also shared between cbl-SL and the *C. Elegans* sli-l cDNA (SEQ ID NO:7).

The invention thus involves in one aspect an isolated cbl-SL polypeptide, the cDNA encoding this polypeptide, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to the invention, isolated nucleic acid molecules that code for a cbl-SL polypeptide include: (a) nucleic acid molecules which hybridize under stringent conditions to a molecule consisting of a nucleic acid of SEQ ID NO: 1 and which code for a cbl-SL polypeptide, (b) deletions, additions and substitutions of (a) which code for a respective cbl-SL polypeptide, (c) nucleic acid molecules that differ from the nucleic acid molecules of (a) or (b) in codon sequence due to the degeneracy of the genetic code, and (d) complements of (a), (b) or (c).

Homologs and alleles of the cbl-SL nucleic acids of the invention can be identified by conventional techniques. Thus, an aspect of the invention is those nucleic acid sequences which code for cbl-SL polypeptides and which hybridize to a nucleic acid molecule consisting of the coding region of SEQ ID NO:1, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15 M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of cbl-SL nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO: 1 and SEQ ID NO:2, respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://wwww.ncbi.nlm.nih.gov. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for cbl-SL related genes, such as homologs and alleles of cbl-SL, a Southern blot may be performed using the foregoing conditions, together with a radioactive probe. After washing the membrane to which the DNA is finally transferred, the membrane can be placed against X-ray film or a phosphoimager plate to detect the radioactive signal.

Given that the expression of the cbl-SL gene is abundant in certain human tissues, and given the teachings herein of a full-length human cbl-SL cDNA clone, other mammalian sequences such as the mouse cDNA clone corresponding to the human cbl-SL gene can be isolated from a cDNA library prepared from one or more of the tissues in which cbl-SL expression is abundant, using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating cbl-SL polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO: 1 or SEQ ID NO:3 or complements of thereof. A unique fragment is one that is a 'signature' for the larger nucleic acid. For example, the unique fragment is long enough to assure that its precise sequence is not found in molecules within the human genome outside of the cbl-SL nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank accession numbers listed in Table 1 (AA113289, AA112513, F22931*, X89223, X57110, U26710) or other previously published sequences as of the filing date of this application.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the cbl-SL polypeptides, useful, for example, in the preparation of antibodies, immunoassays or therapeutic applications. Unique fragments further can be used as antisense molecules to inhibit the expression of cbl-SL nucleic acids and polypeptides respectively.

As will be recognized by those skilled in the art, the size of the unique fragment will depend upon its conservancy in the genetic code. Thus, some regions of SEQ ID NO: 1 or SEQ ID NO:3 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 1547, or SEQ ID NO:3 beginning at nucleotide 1 and ending at nucleotide 1422, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a cbl-SL polypeptide, to decrease cbl-SL activity. When using antisense preparations of the invention, slow intravenous administration is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO: 1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med* 1(11): 1116–1118, 1995). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although, SEQ ID No: 1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO: 1. Similarly, antisense to allelic or homologous cbl-SL cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These to oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding cbl-SL polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for cbl-SL proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *E. coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the. 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding cbl-SL polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (Mol. Cell. Biol. 16:47104716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, cbl-SL cDNA sequence containing expression vectors, to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The invention also permits the construction of cbl-SL gene "knock-outs" in cells and in animals, providing materials for studying certain aspects of cbl-SL activity.

The invention also provides isolated polypeptides (including whole proteins and partial proteins), encoded by the foregoing cbl-SL nucleic acids, and include the polypeptide of SEQ ID NO:2 and unique fragments thereof. Such polypeptides are useful, for example, alone or as fusion proteins that can associate with a tyrosine kinase to form a complex, and regulate a cell's growth, differentiation and proliferation, to generate antibodies, as components of an immunoassay, etc. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of an cbl-SL polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length, 474 amino acids long). Virtually any segment of SEQ ID NO:2, excluding the ones that share identity with it (the polypeptides encoded by the nucleic acids of SEQ ID NOs:4, 5, 6, 7, 8 and 9) that is 9 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof (e.g., a tyrosine kinase phosphatase, other signalling molecules), selective binding to receptors (e.g., the EGF receptor), association with certain adapter molecules (e.g., Grb2), and the non-association with other adapter molecules (e.g., Nck). One important activity is the ability to act as a signature for identifying the polypeptide. Another % is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the cbl-SL polypeptides described above. As used herein, a "variant" of a cbl-SL polypeptide is a polypeptide which contains one or more modification to the primary amino acid sequence of a cbl-SL polypeptide. Modifications which create a cbl-SL polypeptide variant are typically made to the nucleic acid which encodes the cbl-SL polypeptide, and can include deletions, point mutations, truncations, amino acid substitutions and addition of amino acids or non-amino acid moieties to: 1) reduce or eliminate an activity of a cbl-SL polypeptide; 2) enhance a property of a cbl-SL polypeptide, such as protein stability in an expression system or the stability of protein-protein binding; 3) provide a novel activity or property to a cbl-SL polypeptide, such as addition of an antigenic epitope or addition of a detectable moiety; or 4) to provide equivalent or better binding to a cbl-SL polypeptide receptor or other molecule (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the cbl-SL amino acid sequence. One of skill in the art will be familiar with methods for predicting the effect on protein conformation of a change in protein sequence, and can thus "design" a variant cbl-SL polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

Variants can include cbl-SL polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a cbl-SL polypeptide by eliminating proteolysis by proteases in an expression system (e.g., dibasic amino acid residues in yeast expression systems in which KEX2 protease activity is present).

Mutations of a nucleic acid which encodes a cbl-SL polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant cbl-SL polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a cbl-SL gene or cDNA clone to enhance expression of the polypeptide.

The skilled artisan will realize that conservative amino acid substitutions may be made in cbl-SL polypeptides to provide functionally equivalent variants of the foregoing polypeptides, i.e, the variants retain the functional capabilities of the cbl-SL polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the cbl-SL polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of cbl-SL polypeptides, i.e., variants of cbl-SL polypeptides which retain the function of the natural cbl-SL polypeptides, are contemplated by the invention. Conservative amino-acid substitutions in the amino acid sequence of cbl-SL polypeptides to produce functionally equivalent variants of cbl-SL polypeptides typically are made by alteration of a nucleic acid encoding cbl-SL polypeptides (SEQ ID NOs: 1,3). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a cbl-SL polypeptide. The activity of functionally equivalent fragments of cbl-SL polypeptides can be tested by cloning the gene encoding the altered cbl-SL polypeptide into a bacterial or mammalian expression vector, introducing the vector into an appropriate host cell, expressing the altered cbl-SL polypeptide, and testing for a functional capability of the cbl-SL polypeptides as disclosed herein (e.g., selective binding to the EGF receptor, Grb-2, etc.).

The invention as described herein has a number of uses, some of which are described to elsewhere herein. First, the invention permits isolation of cbl-SL polypeptides. A variety of methodologies well-known to the skilled practitioner can be utilized to obtain isolated cbl-SL molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of cbl-SL mRNA in cell-free extracts such as the reticulocyte lysate system also may be used to produce cbl-SL polypeptides. Those skilled in the art also can readily follow known methods for isolating cbl-SL polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from cbl-SL polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The isolation of the cbl-SL cDNA also makes it possible for the artisan to diagnose a disorder characterized by an aberrant expression of cbl-SL. These methods involve determining expression of the cbl-SL gene, and/or cbl-SL polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted cbl-SL protein.

The invention also embraces isolated peptide binding agents which, for example, can be antibodies or fragments of antibodies ("binding polypeptides"), having the ability to selectively bind to cbl-SL polypeptides (e.g., SEQ ID NOs: 2 and 10). Antibodies include polyclonal and monoclonal antibodies, prepared according to conventional methodology. In certain embodiments, the invention excludes binding agents (e.g., antibodies) that bind to the polypeptides encoded for by the nucleic acids of SEQ ID NOs: 4, 5, 6, 7, 8 and 9.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to cbl-SL polypeptides, and complexes of both cbl-SL polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the cbl-SL polypeptide or a complex of cbl-SL and a binding partner. This process can be repeated through several cycles of reselection of phage that bind to the cbl-SL polypeptide or complex. Repeated rounds lead to enrichment of phage bearing particular sequences. DNA sequence analysis can be conducted to identify the sequences of the expressed polypeptides. The minimal linear portion of the sequence that binds to the cbl-SL polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the cbl-SL polypeptides. Thus, the cbl-SL polypeptides of the invention, or a fragment thereof, or complexes of cbl-SL and a binding partner can be used to screen peptide libraries, including phage display libraries, to identify and select peptide binding partners of the cbl-SL polypeptides of the invention. Such molecules can be used, as described, for screening assays, for purification protocols, for interfering directly with the functioning of cbl-SL and for other purposes that will be apparent to those of ordinary skill in the art.

A cbl-SL polypeptide, or a fragment thereof, also can be used to isolate their native binding partners. Isolation of binding partners may be performed according to well-known methods. For example, isolated cbl-SL polypeptides (that include cbl-SL phosporylated polypeptides) can be attached to a substrate, and then a solution suspected of containing an cbl-SL binding partner may be applied to the substrate. If the binding partner for cbl-SL polypeptides is present in the solution, then it will bind to the substrate-bound cbl-SL polypeptide. The binding partner then may be isolated. Other proteins which are binding partners for cbl-SL, may be isolated by similar methods without undue experimentation.

Figure 7:
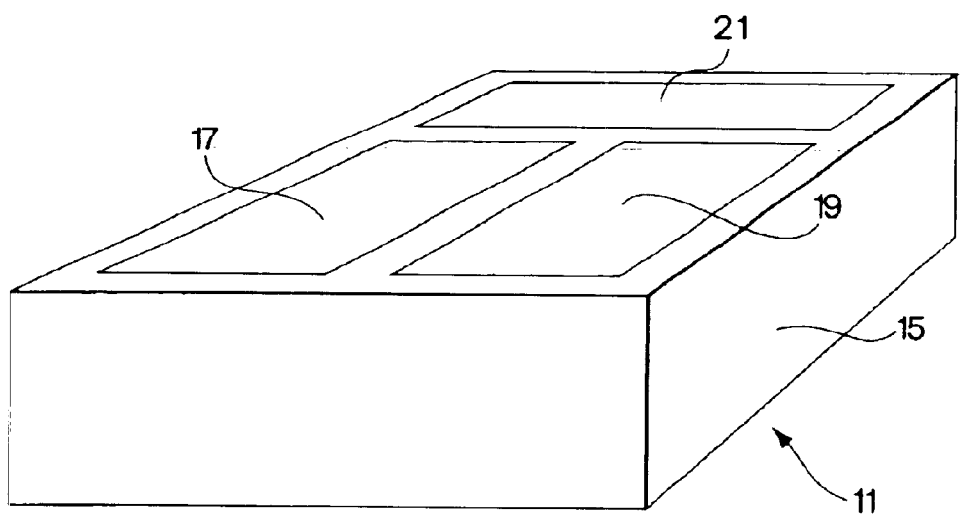
FIG. 7 depicts a kit comprising an agent of the invention (e.g., anti-cbl-SL Abs, cbl-SL epitopes, etc.), a control agent, and instructions for utilizing such agents in diagnostic or therapeutic applications.

The invention also provides novel kits which could be used to measure the levels of the nucleic acids of the invention, expression products of the invention or anti-cbl-SL antibodies. In the case of nucleic acid detection, pairs of primers for amplifying cbl-SL nucleic acids can be included. The preferred kits would include controls such as known amounts of nucleic acid probes, cbl-SL epitopes (such as cbl-SL expression products) or anti-cbl-SL antibodies, as well as instructions or other printed material. In certain embodiments the printed material can characterize risk of developing a cancer based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with cbl-SL protein and a container containing labeled anti-human IgG antibodies. A well of the plate is contacted with, for example, serum, washed and then contacted with the anti-IgG antibody. The label is then detected. A kit embodying features of the present invention, generally designated by the numeral 11, is illustrated in FIG. 7. Kit 11 is comprised of the following major elements: packaging 15, an agent of the invention 17, a control agent 19 and instructions 21. Packaging 15 is a box-like structure for holding a vial (or number of vials) containing an agent of the invention 17, a vial (or number of vials) containing a control agent 19, and instructions 21. Individuals skilled in the art can readily modify packaging 15 to suit individual needs.

The invention also embraces a method of screening for the presence of a carcinoma in a subject suspected of having a carcinoma. The method involves (a) characterizing cbl-SL nucleic acid sequences in a test sample, wherein the test sample is obtained from a tissue of the subject, and (b) comparing the cbl-SL nucleic acid sequences of the test sample to cbl-SL nucleic acid sequences of a control sample (wild-type or mutant). An observed alteration or match in a cbl-SL nucleic acid sequence in the test sample as compared to cbl-SL nucleic acid sequences in the control sample, is indicative of the presence of carcinoma in the subject.

By observed "alteration", it is meant that a cbl-SL nucleic acid sequence in the test sample is compared to a control sequence in the control sample, with the control sequence being a wild-type cbl-SL nucleic acid according to the invention (e.g., SEQ ID NO:1 or 3), and the test sample cbl-SL sequence is different to the control sample cbl-SL sequence. Alternatively, an observed "match" may be detected when a cbl-SL nucleic acid sequence in the test sample is compared to a control sequence in the control sample, with the control sequence being a mutant cbl-SL nucleic acid, and the test sample cbl-SL sequence is found identical to the control sample cbl-SL sequence. Appropriate differences and/or matches in the sequences can be determined with no more than routine experimentation by those of ordinary skill in the art.

The invention also provides methods to measure the level of cbl-SL expression in a subject. This can be performed by first obtaining a test sample from the subject. The test sample can be tissue or biological fluid. Tissues include brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. In certain embodiments, test samples originate from colon, breast and prostate tissues, and biological fluids include blood, saliva and urine. Both invasive and non-invasive techniques can be used to obtain such samples and are well documented in the art. At the molecular level both PCR and Northern blotting can be used to determine the level of cbl-SL mRNA using products of this invention described earlier, and protocols well known in the art that are found in references which compile such methods. At the protein level, cbl-SL expression can be determined using either polyclonal or monoclonal anti-cbl-SL sera in combination with standard immunological assays. The preferred methods will compare the measured level of cbl-SL expression of the test sample to a control. A control can include a known amount of a nucleic acid probe, a cbl-SL epitope (such as a cbl-SL expression product), or a similar test sample of a subject with a control or 'normal' level of cbl-SL expression.

The invention also embraces a method for treating subjects expressing a mutant cbl-SL. It involves first determining whether the subject, and in particular a specific tissue of the subject, expresses a mutant cbl-SL or a wild-type cbl-SL. As used herein, "wild-type" refers generally to a molecule which is ordinary, common, without defect or affect, and not mutant. An ordinary molecule, also refers generally to sequences or structures that, while they may vary from a canonical sequence or structure, comprise neutral polymorphisms and do not vary in function from a molecule having a non-mutant sequence or structure. According to the invention, a wild-type cbl-SL is, for example, a nucleic acid of SEQ ID NO: 1 and its encoded polypeptide presented as SEQ ID NO:2). Wild-type cbl-SL is capable of binding to, for example, the intact Epidermal Growth Factor (EGF, a.k.a. Grb-2) receptor without EGF stimulation, or to the Grb-2 SH2 domain only after EGF stimulation, or to a tyrosine kinase phosphatase, and does not bind to N-terminal SH3 domains of Nck. Conversely, a "mutant" cbl-SL typically has undergone a nucleic acid substitution that results in a non-conservative amino acid substitution at the polypeptide level that changes the cbl-SL's binding characteristics, thus rendering, for example, a proliferative phenotype to the cell. If the tissue of the subject expresses a mutant cbl-SL, then an effective amount of a wild-type cbl-SL may be administered to the subject in order to increase expression of wild-type cbl-SL in the affected tissue of the subject. Preferred tissues that may benefit from the foregoing therapeutic regimen include tissues with predominant cbl-SL expression, i.e., non-hematopoietic organs, particularly those with a large epithelial component.

The mode of administration and dosage of the agent will vary with the particular stage of the condition being treated, the age and physical condition of the subject being treated, the duration of the treatment, the nature of the concurrent therapy (if any), the specific route of administration, and the like factors within the knowledge and expertise of the health practioner. In preferred embodiments of the invention cancers expressing a mutant cbl-SL include: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer, sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In other embodiments cancers expressing cbl-SL are cancers aberrantly expressing cbl-SL. Aberrant expression is expression of a mutant cbl-SL.

In certain embodiments the agent can be administered, as mentioned earlier, in combination with other anti-cancer agents such as: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estrarustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan;

Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Taxol; Taxotere; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The invention also embraces methods for inhibiting cell proliferation by contacting a cell expressing a mutant cbl-SL with the isolated nucleic acids of the invention, or expression products thereof, in an amount effective to increase cbl-SL activity in the cell and restore proper (i.e., to wild-type standards) cell cycle regulation. Such methods can be very useful in regulating cancerous cell proliferation both in vivo and in vitro. The preferred agent is a wild-type cbl-SL or an active fragment thereof.

The pharmaceutical preparations, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a decrease in cell proliferation.

Generally, doses of active compounds of the present invention would be from about 0.01 mg/kg per day to 1000 mg/kg per day. It is expected that doses ranging from 50–500 mg/kg will be suitable. A variety of administration routes are available. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule. When peptides are used therapeutically, in certain embodiments a desirable route of administration is by pulmonary aerosol. Techniques for preparing aerosol delivery systems containing peptides are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 13th edition, 1990, pp 1694–1712; incorporated by reference). Those of skill in the art can readily determine the various parameters and conditions for producing antibody or peptide aerosols without resort to undue experimentation.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The cbl-SL polypeptides or fragments thereof may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Cbl-SL polypeptides preferably are produced recombinantly, although such polypeptides may be isolated from biological extracts. Recombinantly produced cbl-SL polypeptides include chimeric proteins comprising a fusion of a cbl-SL protein with another polypeptide, e.g., a polypeptide capable of providing or enhancing protein-protein binding, sequence specific nucleic acid binding (such as GAL4), enhancing stability of the cbl-SL polypeptide under assay conditions, or providing a detectable moiety, such as green fluorescent protein. A polypeptide fused to a cbl-SL polypeptide or fragment may also provide means of readily detecting the fusion protein, e.g., by immunological recognition or by fluorescent labeling.

The invention also useful in the generation of transgenic non-human animals. As used herein, "transgenic non-human animals" includes non-human animals having one or more exogenous nucleic acid molecules incorporated in germ line cells and/or somatic cells. Thus the transgenic animal include "knockout" animals having a homozygous or heterozygous gene disruption by homologous recombination, animals having episomal or chromosomally incorporated expression vectors, etc. Knockout animals can be prepared by homologous recombination using embryonic stem cells as is well known in the art. The recombination may be facilitated using, for example, the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to cbl-SL nucleic acid molecules to increase expression of cbl-SL in a regulated or conditional manner. Trans-acting negative regulators of cbl-SL activity or expression also can be operably linked to a conditional promoter as described above. Such frans-acting regulators include antisense cbl-SL nucleic acids molecules, nucleic acid molecules which encode dominant negative cbl-SL molecules, ribozyme molecules specific for cbl-SL nucleic acids, and the like. The transgenic non-human animals are useful in experiments directed toward testing biochemical or physiological effects of diagnostics or therapeutics for conditions characterized by increased or decreased cbl-SL expression. Other uses will be apparent to one of ordinary skill in the art.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention also embraces a method for downregulating (or inhibiting) expression of a tyrosine kinase in a cell. The method involves contacting a cell expressing a tyrosine kinase with a cbl-SL polypeptide, in an amount effective to downregulate expression of the tyrosine kinase in the cell. The term "downregulating (or inhibiting) expression" is as described earlier. "Contacting," as used herein, refers to intracellular binding of a cbl-SL poypeptide with a tyrosine kinase. Preferably, cbl-SL polypeptides are produced intracellularly by the cell, following introduction into the cell of cbl-SL nucleic acids of the invention. Cbl-SL polypeptides, however, may be directly introduced into the cell expressing a tyrosine kinase using mehtods well known in the art, some of which are described elsewhere herein. Preferred cbl-SL polypeptides include the polypeptides of claim 12. In certain embodiments, the tyrosine kinase is selected from the group consisting of a receptor tyrosine kinase, a non-receptor tyrosine kinase, and any of the foregoing tyrosine kinases in complex with another agent. In one embodiment, the tyrosine kinase is ligand activated. In any of the foregoing embodiments, the tyrosine kinase can be phosphorylated. In certain embodiments, the cbl-SL and tyrosine kinase further complexes with an intermediate adapter molecule (e.g., Grb-2).

The invention further provides efficient methods of identifying agents or lead compounds for agents active at the level of a cbl-SL or cbl-SL fragment dependent cellular function. In particular, such functions include interaction with other polypeptides or fragments thereof (e.g., a tyrosine kinase—including selective binding to e.g., the EGF receptor, other signalling molecules, etc.), certain intermediate adapter molecules (e.g., Grb2), and the absence of association with other intermediate adapter molecules (e.g., Nck). Generally, the screening methods involve assaying for compounds which interfere with cbl-SL activity (such as cbl-SL binding to the EGF receptor), although compounds which enhance cbl-SL activity also can be assayed using the screening methods. Such methods are adaptable to automated, high throughput screening of compounds. The target therapeutic indications for pharmacological agents detected by the screening methods are limited only in that the target cellular function be subject to modulation by alteration of the formation of a complex comprising a cbl-SL polypeptide or fragment thereof and one or more natural cbl-SL binding targets, such as a tyrosine kinase (e.g., EGFR: the EGF receptor, etc). Target indications include cellular processes modulated by cbl-SL (such as the cell cycle, cell migration, cell differentiation, cell proliferation, etc.), and affected by cbl-SL's ability to form complexes with other molecules and polypeptides. The specific binding is typically compared to controls. Controls typically include all of the reagents in the mixture except the candidate agent.

A wide variety of assays for agents are provided, including, labeled in vitro protein-protein binding assays, electrophoretic mobility shift assays, immunoassays, cell-based assays such as two- or three-hybrid screens, expression assays, etc. For example, two-hybrid screens are used to rapidly examine the effect of transfected nucleic acids on the intracellular binding of cbl-SL or cbl-SL fragments to specific intracellular targets (e.g. a tyrosine kinase). The transfected nucleic acids can encode, for example, combinatorial peptide libraries or cDNA libraries. Convenient reagents for such assays, e.g., GAL4 fusion proteins, are known in the art. An exemplary cell-based assay involves transfecting a cell with a nucleic acid encoding a cbl-SL polypeptide fused to a GAL4 DNA binding domain and a nucleic acid encoding a reporter gene operably linked to a gene expression regulatory region, such as one or more GAL4 binding sites. Activation of reporter gene transcription occurs when the cbl-SL and reporter fusion polypeptides bind such as to enable transcription of the reporter gene. Agents which modulate a cbl-SL polypeptide mediated cell function are then detected through a change in the expression of reporter gene. Methods for determining changes in the expression of a reporter gene are known in the art.

Cbl-SL fragments used in the methods, when not produced by a transfected nucleic acid are added to an assay mixture as an isolated polypeptide. Cbl-SL polypeptides preferably are produced recombinantly, although such polypeptides may be isolated from biological extracts. Recombinantly produced cbl-SL polypeptides include chimeric proteins comprising a fusion of a cbl-SL protein with another polypeptide, e.g., a polypeptide capable of providing or enhancing protein-protein binding, sequence specific nucleic acid binding (such as GAL4), enhancing stability of the cbl-SL polypeptide under assay conditions, or providing a detectable moiety, such as green fluorescent protein or Flag epitope.

The assay mixture is comprised, in some embodiments, of a natural intracellular cbl-SL binding target capable of interacting with cbl-SL. While natural cbl-SL binding targets may be used, it is frequently preferred to use portions (e.g., peptides or nucleic acid fragments) or analogs (i.e., agents which mimic the cbl-SL binding properties of the natural binding target for purposes of the assay) of the cbl-SL binding target so long as the portion or analog provides binding affinity and avidity to the cbl-SL fragment measurable in the assay.

The assay mixture also comprises a candidate agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, anti-microbial agents, and the like may also be used.

The mixture of the foregoing assay materials is incubated under conditions whereby, but for the presence of the candidate pharmacological agent, the cbl-SL polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the cbl-SL polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of cbl-SL polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., to epitope tag such as the FLAG epitope, enzyme tag such as horseseradish peroxidase, etc.). The label may be bound to a cbl-SL binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides cbl-SL-specific binding agents, methods of identifying and making such agents, and their use in diagnosis, therapy and pharmaceutical development. For example, cbl-SL-specific pharmacological agents are useful in a variety of diagnostic and therapeutic applications, especially where disease or disease prognosis is associated with altered cbl-SL binding characteristics. Novel cbl-SL-specific binding agents include cbl-SL-specific antibodies, cell surface receptors, and other natural intracellular and extracellular binding agents identified with assays such as two hybrid screens, and non-natural intracellular and extracellular binding agents identified in screens of chemical libraries and the like.

In general, the specificity of cbl-SL binding to a specific molecule is determined by binding equilibrium constants. Targets which are capable of selectively binding a cbl-SL polypeptide preferably have binding equilibrium constants of at least about $10^7$ $M^{-1}$, more preferably at least about $10^8$ $M_{-1}$, and most preferably at least about $10^9$ $M^{-1}$. The wide variety of cell based and cell free assays may be used to demonstrate cbl-SL-specific binding. Cell based assays include one, two and three hybrid screens, assays in which cbl-SL-mediated transcription is inhibited or increased, etc. Cell free assays include cbl-SL-protein binding assays, immunoassays, etc. Other assays useful for screening agents which bind cbl-SL polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

EXAMPLES

Experimental Procedures

Screening of the cDNA Library

A pancreatic adenocarcinoma from Stratagene (La Jolla, Calif., cat #937208) was screened according to manufacturers recommendation using the insert of I.M.A.G.E. clone ID 526956 from ATCC (Manassas, Va.). Hybridization was performed in QuikHyb (Stratagene, La Jolla, Calif., cat #201220) under stringent hybridization conditions. Using standard methodology (*Molecular Cloning*: A Laboratory Manual, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York), individual cDNA clones were subjected to 3–4 rounds of amplification and purification under the same hybridization conditions.

After excision from the vector and subcloning of inserts into the plasmid forms, several clones were sequenced by the Brigham and Women's Hospital Automated Sequencing and Genotyping Facility. Molecular biological techniques such as restriction enzyme treatment, subcloning, DNA extraction, bacterial culture and purification of DNA fragments were performed according to methods well known in the art. Computer analyses of protein and DNA sequences was done using the GCG "Idea" program (Kaneshisa, National Cancer Institute, Frederick, Md., 1986). Restriction endonucleases, expression vectors, and modifying enzymes were purchased from commercial sources (Gibco-BRL). Sequencing vectors for DNA were purchased from Stratagene (La Jolla, Calif.). Oligonucleotide probes were purchased from Lofstrand Labs Limited (Gaithersburg, Md.). The sequence of the resulting cbl-SL full length clone was confirmed on more independent clones.

Cbl-SL Expression

The Tissue blot was purchased from Clontech (Palo Alto, Calif.; cat #7770-1) and was hybridized using identical hybridization conditions employed in the initial cDNA library screen. The RNA Blot used in the Northern was also a Clontech product (cat #7759-1) that was also subjected to the same hybridization procedures as described above.

Antibodies

The monoclonal antibodies used in this work were 4G10 [anti-Tyr(P)], mouse IgG2a, gift of B. Druker, Oregon Health Science University, Portland, Oreg.) (Druker et al., N. Engl. J. Med., 1989, 321:1383–1391), 12CA5 [anti-influenza hemagglutinin (HA) epitope tag], mouse IgG2b) (Wilson et al., Cell, 1984, 37:767–778), and OKT8 (anti-human CD8, mouse IgG2b used as negative control for anti-HA; American Type Culture Collection, Manassas, Va.). Polyclonal rabbit antibodies against Grb2 (sc-255), Cbl (sc-170), Cbl-b (sc-1705: cross-reacts with Cbl and Cbl-SL; this paper and data not shown), and EGFR (sc-03) were from Santa Cruz Biotechnology Inc. (Santa Cruz, Calif.).

Glutathione S-Transferase (GST) Fusion Proteins

Cbl-SL nucleic acid sequences were placed into pGEX4T.1 vector (Pharmacia Biotech, Inc.) in-frame with glutathione S-transferase (GST). Fusion proteins were affinity-purified on glutathione-Sepharose beads (Pharmacia Biotech, Inc.) using art recognized methodology(see e.g., Fukazawa et al., J. Biol. Chem., 1995, 270:19141–19150; Reedquist et al., Proc. Natl. Acad. Sci. U.S.A., 1994, 91:4135–4139; Reedquist et al., J. Biol. Chem., 1996, 271:8435–8442). Multiple independent bacterial colonies producing cbl-SL, c-cbl, Grb-2, Grb2-SH2, Fyn-SH3, and p85-SH3 fusion proteins were tested. Other/alternative GST-fusion proteins also used in this study have been described previously: GST and GST-Fyn-SH3 in pGEX-2T.K; GST-Src-SH3 and GST-Crk-SH3 in pGEX-2T; GST-Grb2, GST-Grb2-SH2, and GST-p85-SH3 in pGEX-3X (Fukazawa et al., J. Biol. Chem., 1995, 270:19141–19150; Reedquist et al., J. Biol. Chem., 1996, 271:8435–8442). GST-Nck-SH3 (containing N-terminal two SH3 domains of Nck) (Lu et al., Curr. Biol., 1997, 7:85–94) was kindly provided by Bruce Mayer (Children's Hospital, Boston, Mass.). GST fusion proteins were purified as previously described (Reedquist et al., Proc. Natl. Acad. Sci. USA., 1994, 91:4135–4139).

Binding Reactions, Immunoprecipitations, Gel Electrophoresis, and Immunoblotting Binding reactions were typically carried out with 20 μg of purified GST fusion protein and lysate from cells for 1 h (or as indicated) at 4° C. For immunoprecipitations, cell lysate was incubated with antibodies for 1 h (or as indicated) at 4° C., followed by 20 μl of protein A-Sepharose 4B beads (Pharmacia Biotech, Inc., Piscataway, N.J.) for 1 h. In all cases, beads were washed six times in lysis buffer (Fukazawa, T. et al., J Biol Chem, 1995, 270:19141–19150). Bound proteins were eluted from washed beads in Laemmli sample buffer with 2-mercaptoethanol and resolved by sodium dodecyl sulfate-polyacrylamide gel electrophoresis.

Polypeptides were transferred to PVDF membranes (Immunobilon-P, Millipore Corp., Bedford, Mass., or polyscreen, NEN-Life Sciences, Inc., Boston, Mass.), and immunoblotted using protein A-horseradish peroxidase (PA-HRPO) (Cappel-Organon Technika, Durham, N.C.) as a secondary reagent and enhanced chemiluminescence (ECL) detection (Renaissance™ chemiluminescence reagent and Reflection™ autoradiographic film, NEN-Life Sciences, Inc., Boston, Mass.), as described in Fukazawa, T. et al., J Biol Chem, 1995, 270:19141–19150).

Plasmids, Transient Transfection, EGF Stimulation, and Preparation of Cell Lysates The full-length Cbl-SL cDNA, encoding an N-terminally hemagglutinin (HA) epitope-tagged Cbl-SL protein, was generated by joining five PCR-derived segments via introduced unique restriction sites which did not change the encoded protein. The HA epitope was placed between residues 1 and 2. The full-length cDNA was cloned into pcDNA3 mammalian expression vector (Invitrogen, Carlsbad, Calif.) to yield pcDNA3-HA-Cbl-SL. The pAlterMAX-HA-Cbl expression vector, encoding HA-tagged human Cbl, has been described (Lupher et al., J. Biol. Chem., 1996, 271, 24063–24068). The EGFR expression construct was generated by subcloning a KpnI/SalI restriction fragment from a pUC-based plasmid (kind gift from Wallace Y. Langdon, University of Western Australia, Nedlands, Western Australia) into the pAlterMAX vector (Lupher, et al., J. Biol. Chem., 1998, 52:35273–35281; Lill et al., J. Biol. Chem., 1999, in press).

Figure 8:
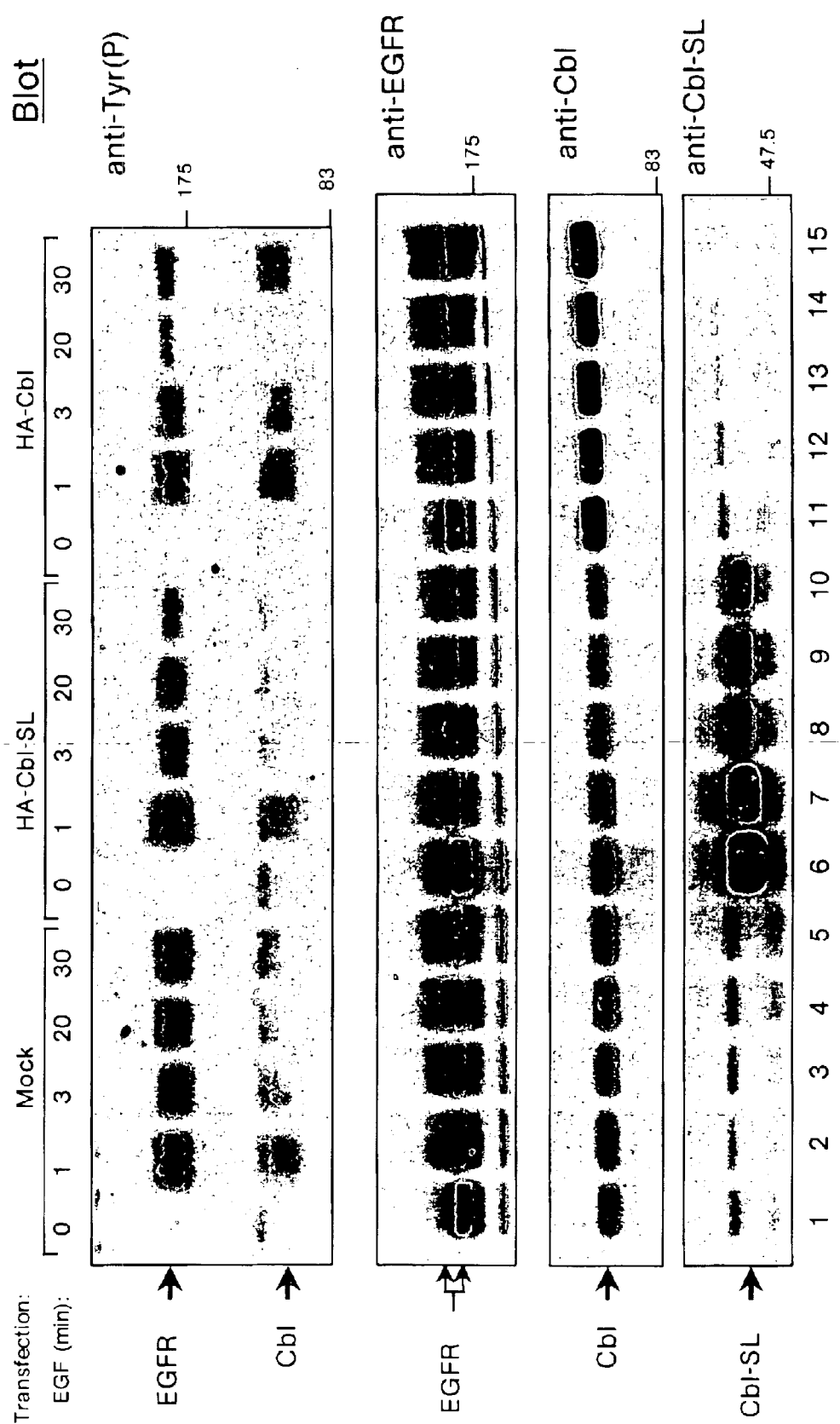
FIG. 8 shows the enhanced down-regulation of the EGF-receptor (EGFR) upon cbl-SL overexpression.

COS-7 and 293 human embryonic kidney (HEK) cells were grown in DMEM (Life Technologies, Inc., Gaithersburg, Md.) supplemented with 10% fetal calf serum (Hyclone Laboratories Inc., Logan, Utah), 20 mM HEPES pH 7.35, 1 mM sodium pyruvate, 1 mM non-essential amino acids, 100 units/ml penicillin and 100 μg/ml streptomycin (all from Life Technologies, Inc.). $4.5 \times 10^5$ COS-7 cells per 10-cm dish were plated overnight in DMEM. The cells were washed and transfected with 2 μg of pcDNA3-HA-Cbl-SL or p-AlterMAX-HA-Cbl using Lipofectamine™ (Life Technologies, Inc.) in OPTI-MEM medium, following the manufacturer's protocol. After 6 hrs, regular DMEM was added. For 293 HEK cells, transient transfection was performed using the calcium phosphate method (Chen & Okayama, Mol Cell Biol, 1987, 7:2745–52) using 1 μg pcDNA3-HA-Cbl-SL or pAlterMAX-HA-Cbl with 0.05 μg pAlterMAX-EGFR expression plasmids. Culture media was replaced at 14–18h following the addition of DNA precipitates. For EGF stimulation of COS-7 or 293 HEK cells, cells were serum-starved for 5–6h (DMEM containing 0.5% instead of 10% FCS), then were incubated for the indicated lengths of time with purified murine EGF (Sigma) at 100 ng/ml. The cells were then rinsed with ice-cold PBS and processed as described below. Typically, 36–48 hr post-transfection the cells were washed with ice-cold phosphate-buffered saline (PBS) and lysed on ice in a buffer consisting of 0.5% Triton X-100 (Fluka), 50 mM Tris pH 7.5, 150 mM NaCl, 1 mM phenylmethylsulfonyl fluoride, 1 mM sodium orthovanadate, 10 mM sodium fluoride, and a cocktail of protease inhibitors (1 μg/ml aprotinin, chymostatin, leupeptin, antipain, and pepstatin A) (Sigma Chemicals Co., St Louis, Mo.). Lysates were rocked at 4° C. for 30 min, centrifuged for 10 min and the total protein concentration was determined using the Bradford assay (BioRad Laboratories, Hercules, Calif.) with bovine serum albumin as the standard. 30 μg of whole cell lysate was subjected to SDS-PAGE on a 6.5% gel. After transfer, the membrane was cut in two parts just below the 175 kDa marker. The upper part was blotted with anti-EGFR antibody, and the lower one was blotted with a mixture of anti-Cbl antibody and anti-Cbl-SL antiserum (FIG. 8). After stripping, both parts were re-probed with the anti-Tyr(P) antibody 4G10; anti-Tyr(P) blot is shown as a single panel (FIG. 8, top panel).

Analysis of Tyrosine Kinase Turnover

The turnover of a tyrosine kinase, e.g., EGF-R in 293 HEK cells expressing endogenous Cbl (mock-transfected)

versus those overexpressing HA-Cbl and/or HA-Cbl-SL, was evaluated by pulse-chase analysis using a modification of the previously reported protocol (Lill, et al., *J. Virol.,* 1997, 71:129–137). In brief, cells were transfected in 10 cm tissue culture dishes by the calcium phosphate technique, to yield subconfluent cultures at 48–72 h post-transfection. Cells were rinsed with methionine-free DMEM and methionine-starved for 2 h at 37° C. by incubation in methionine-free DMEM supplemented with 0.5% dialyzed FBS (Life Technologies, Gaithersburg, Md.). Cells were pulse-labeled by adding 50 µCi/ml EXPRESS labeling mix (NEN/DuPont, Boston, Mass.) for 40 min at 37° C. After three washes in DMEM, the cells were incubated for 2.5 h in chase medium (DMEM supplemented with 0.5% dialyzed FBS and 3 mg/ml L-methionine) to allow newly synthesized EGF-R to undergo post-translational modification, acquire the capacity to bind to ligand, and be transported to the cell surface. One plate from each transfection set was harvested without further EGF stimulation (0 min stimulation). Cells in the remaining plates were incubated in chase medium containing EGF (100 ng/ml) for the indicated times. Lysate preparation, protein quantification, immunoprecipitation, and gel resolution and PVDF membrane immobilization of proteins were performed as described elsewhere herein. The membrane was used first for autoradiography for detection of radiolabeled proteins (BIOMAX-MR film, Eastman Kodak Co., Rochester, N.Y.), and then in anti-EGF-R immunoblotting to confirm the identity of specific radiolabeled proteins as EGF-R. For quantification of tyrosine kinase (e.g., receptor tyrosine kinase) turnover, autoradiograms were scanned using a Hewlett Packard ScanJet4c™ and Corel Draw™ version 6 software. Densitometry was performed using ScionImage for Windows™ software.

Example 1

Generation of Polyclonal Rabbit Antibodies Specific for Cbl-SL

Figure 3A:
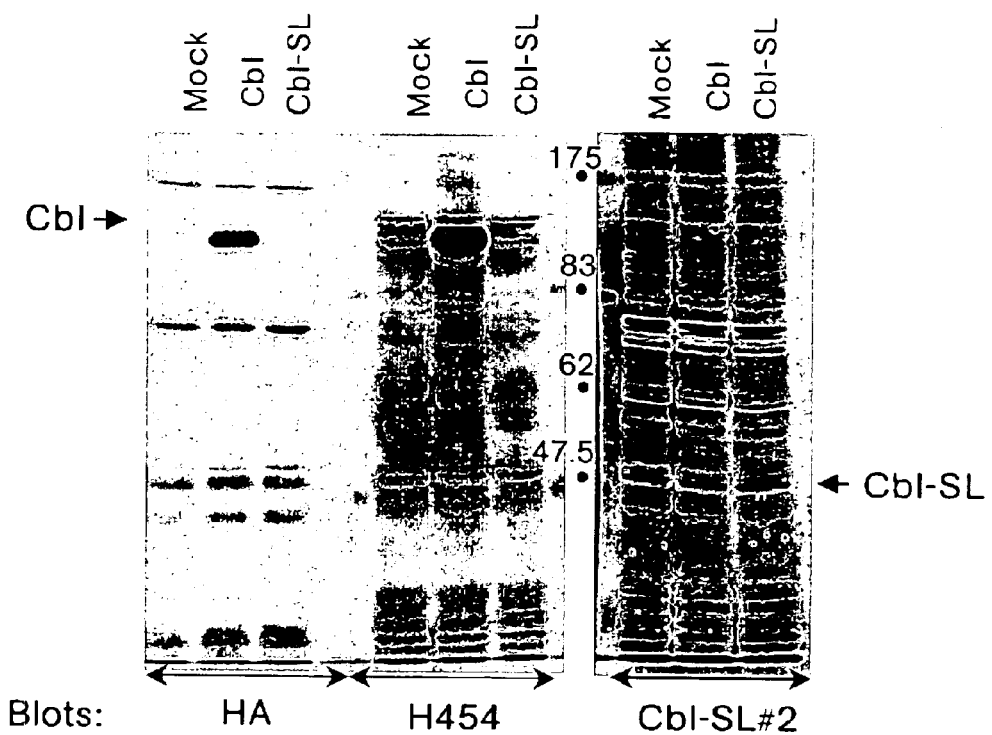
FIGS. 3A and 3B show the specific binding of cbl-SL polyclonal antisera using Western blots.
Figure 3B:
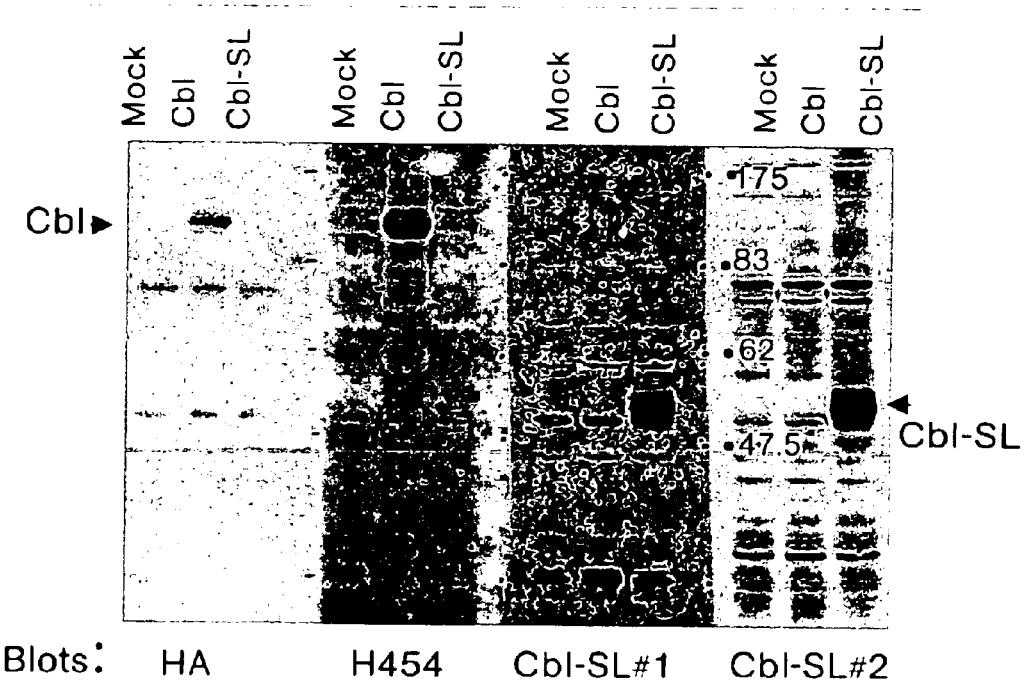
Figure 3C:
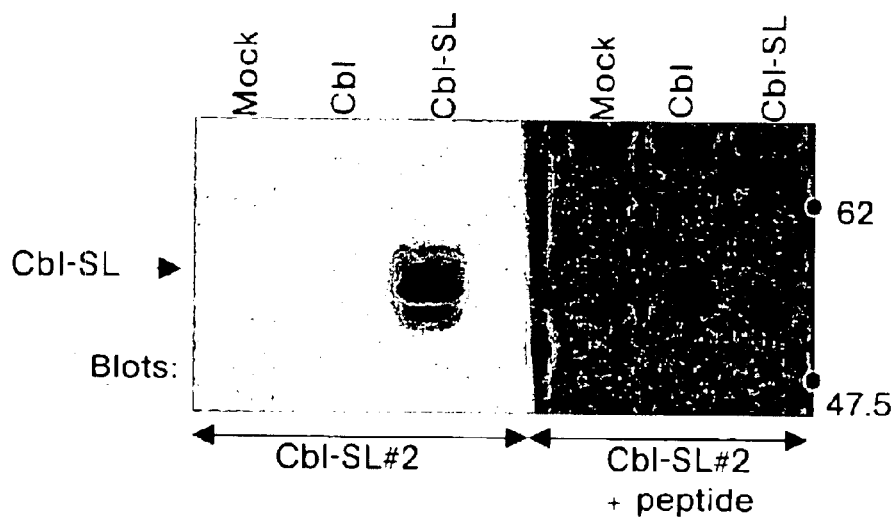
In FIG. 3C, an immunizing peptide was used as a conpetitor.
Figure 3D:
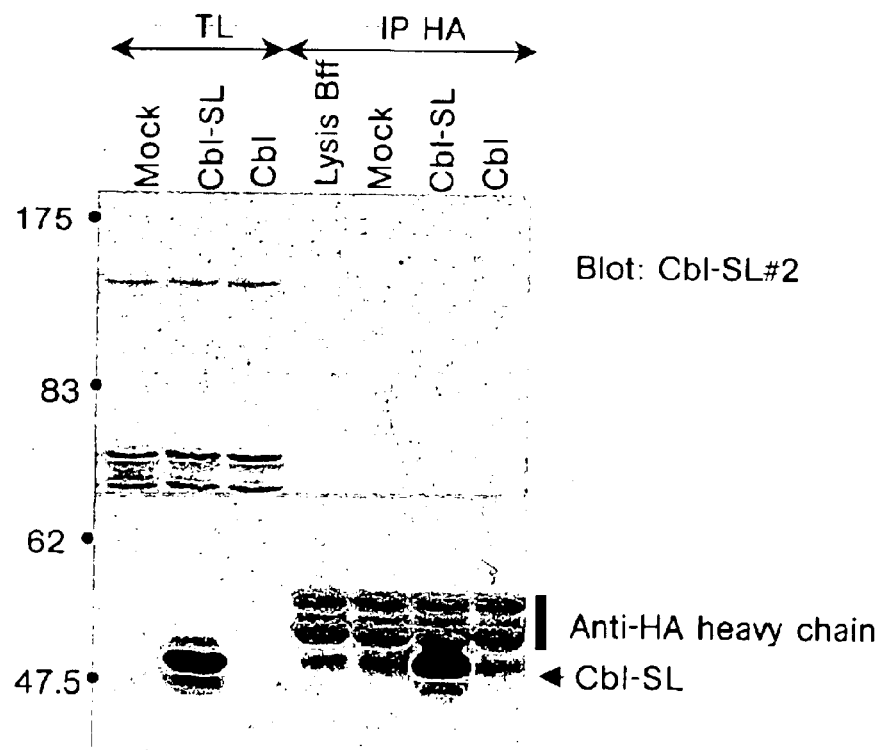
FIG. 3D also shows the specific binding of cbl-SL polyclonal antisera on HA-purified protein lysates.

Cos 7 cells were transiently transfected with pcDNA3 (mock), HA-tagged Cbl-SL (in pcDNA3) or HA-tagged Cbl (in pAlterMax). After 48h, cells were lysed in buffer consisting of 50 mM Tris pH 8.0, 150 mM NaCl, 0.5% Triton 100X, plus a coktail of protease and phosphatase inhibitors. 50 µg of total lysate was loaded in each lane and resolved on a 7.5% SDS-PAGE gel and transferred to a PDVF membrane. The membrane was blocked in gelatin and blotted with the indicated antibodies for 1 h, washed with TBS-Tween and incubated for 30 min with Protein A HRP-conjugate. After 1 min incubation with a chemiluminescent reagent, autoradiographic exposures were taken. The results of this experiment are shown in FIG. 3A. H454 (Santa Cruz) is a polyclonal rabbit anti-Cbl-b antibody which cross-reacts with Cbl (the immunogen corresponds to the N-terminal region of Cbl-b). Anti-Cbl-SL antibody was raised by Zymed Laboratories, Inc. (San Francisco, Calif.) by immunizing rabbits with cbl-SL peptide (SEQ ID NO:10, or aa 445–461 of SEQ ID NO:2) coupled to KLH. Cbl-SL#2 is the serum from the second rabbit after the first immunization and was used at a dilution 1/1000. FIG. 3B depicts the results of an identical experiment, except that two independent anti-Cbl-SL antisera were used. In this second experiment, Cbl-SL#1 and Cbl-SL#2 correspond to the second sera obtained after immunization of the rabbits #1 and #2, respectively. In FIG. 3C, membranes from FIG. 3B were stripped and re-blotted with anti-SL#2 serum in the absence (left membrane) or presence (right membrane) of the immunizing peptide (5 µg/ml) as a competitor. Note the absence of Cbl-SL band in the presence of the peptide. In a different experiment, lysates from mock-transfected, Cbl-SL-transfected and Cbl-transfected Cos 7 cells were immunoprecipitated with the anti-HA antibody (12CA5) and the bound proteins were resolved by SDS-PAGE and transferred to a PDVF membrane. The membrane was blotted with the anti-Cbl-SL#2. In FIG. 3D, the results of this experiment are presented, showing the specificity of the serum for Cbl-SL only. TL=total lysate; IP-HA=anti-HA immunoprecipitates.

Example 2

Tissue Specific Expression of Cbl-SL

Figure 1B:
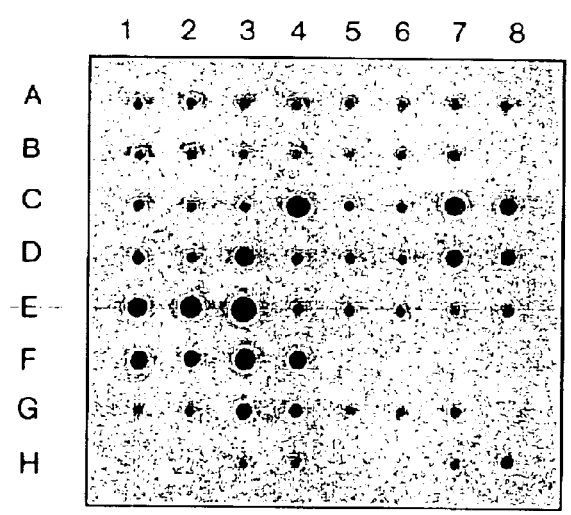

The Cbl-SL EST (clone # 526956, accession # AA112513) was used to generate a 322 bp $^{32}$P-labelled probe to assess the expression Cbl-SL mRNA in various human tissues (FIG. 1B). First, we probed a commercialy obtained 'tissue blot' where mRNA samples from various human tissues have been immobilized on a nylon membrane via dot-blotting. The amount of RNA was normalized based on the expression of several housekeeping genes (manufacturer specifications, Clontech). This 'tissue blot' analysis (FIG. 1B) showed that Cbl-SL mRNA was predominantly expressed in colon (C4), small intestine (E3), stomach (C8), kidney (E1), liver (E2), pancreas (D3), prostate (C7), mammary gland (D8), salivary gland (D7), trachea (F3), appendix (F1) and placenta (F4), with substantially lower levels in a number of other organs. Most notably, the levels of Cbl-SL mRNA were very low to undetectable in several hematopoietic tissues, in particular the thymus (E5), peripheral blood leukocytes (E6), spleen (E4) and bone marrow (E8). In contrast, Cbl mRNA expression was expectedly broad, with relatively high levels in the hematopoietic tissues (FIG. 1A).

Figure 2:
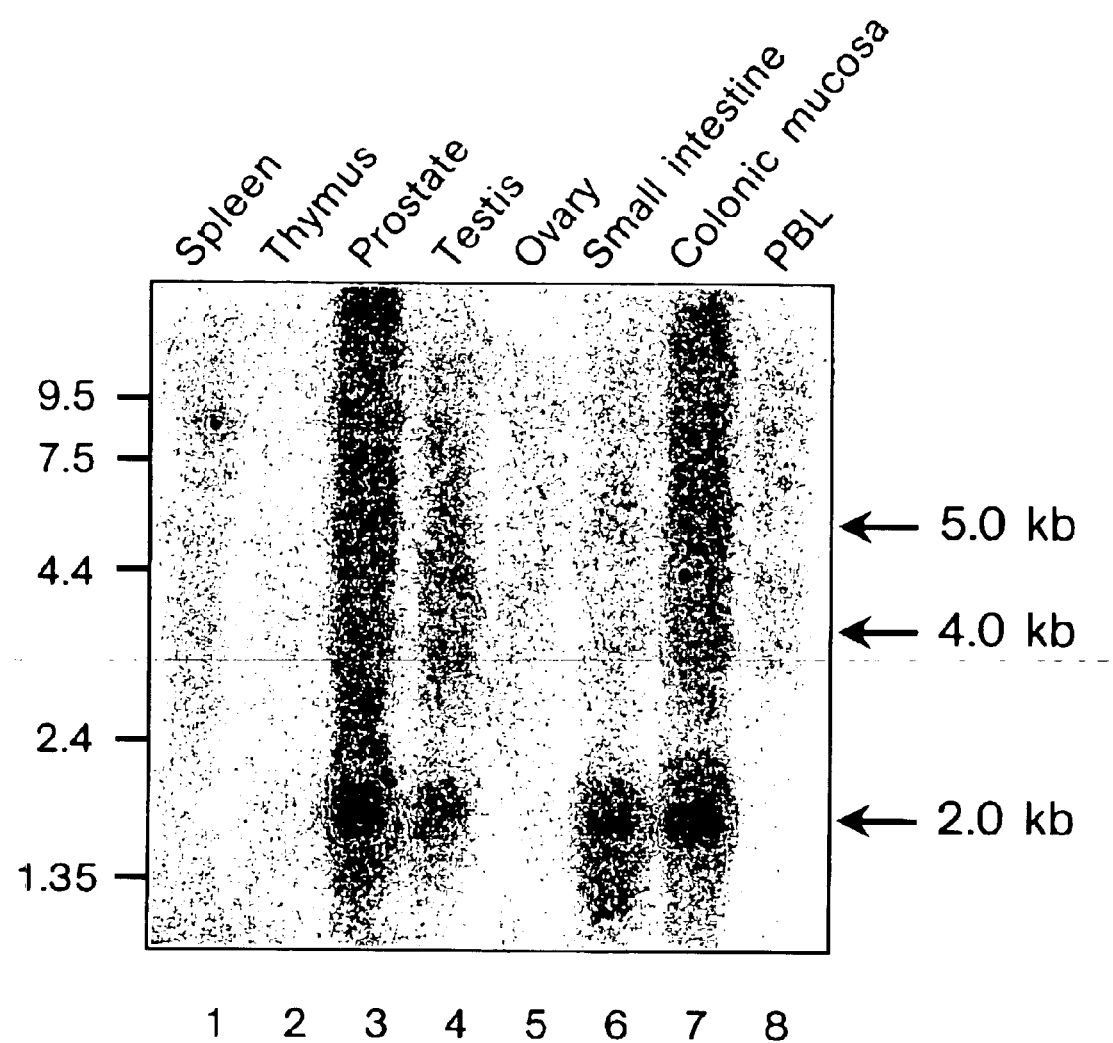
FIG. 2 shows a cbl-SL mRNA expression in a Northern Blot.

Northern blot analysis of selected human tissue RNA samples further confirmed the restricted expression of Cbl-SL (FIG. 2), and in addition showed that the predominant mRNA species was about 2.0 kb, compared to a 11 kb size reported for Cbl (Langdon et al., *J. Virol.,* 1989, 63:5420–5424). Minor mRNA species of approximately 4 and 5 kb were observed upon longer exposure of the blot. Collectively, these results demonstrate that the pattern of Cbl-SL mRNA expression is distinct from that of Cbl, and is relatively selective with predominant expression in non-hematopoietic organs, particularly those with a large epithelial component.

Example 3

A Candidate Endogenous Cbl-SL Polypeptide

Figure 4A:
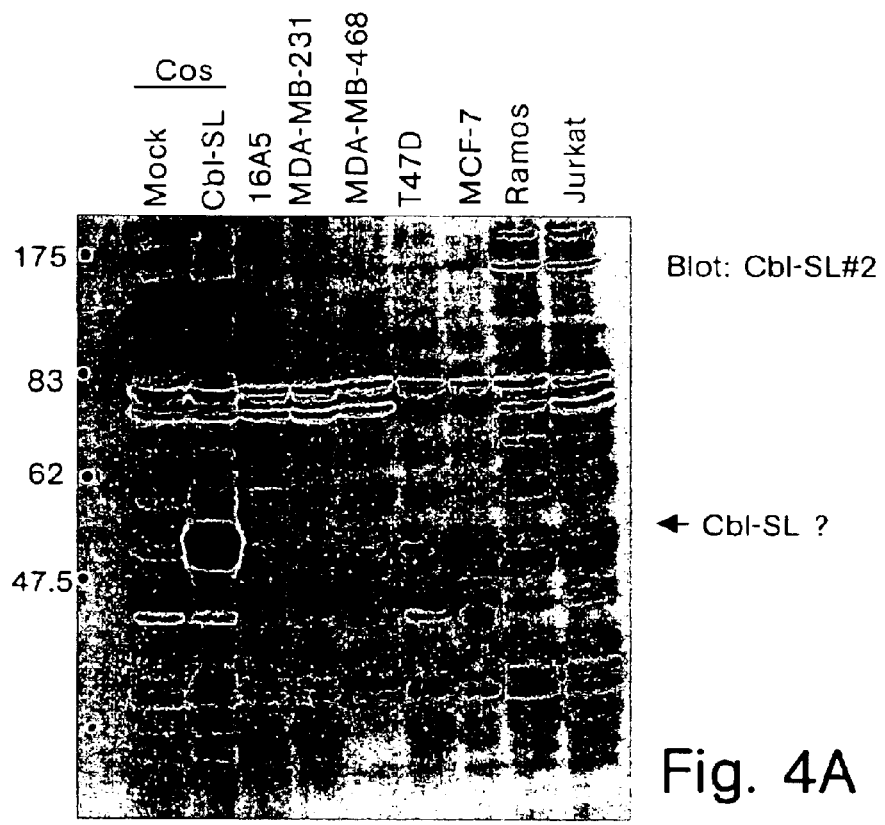
FIG. 4A depicts a ~50 kd cbl-SL protein band in a Western blot.
Figure 4B:
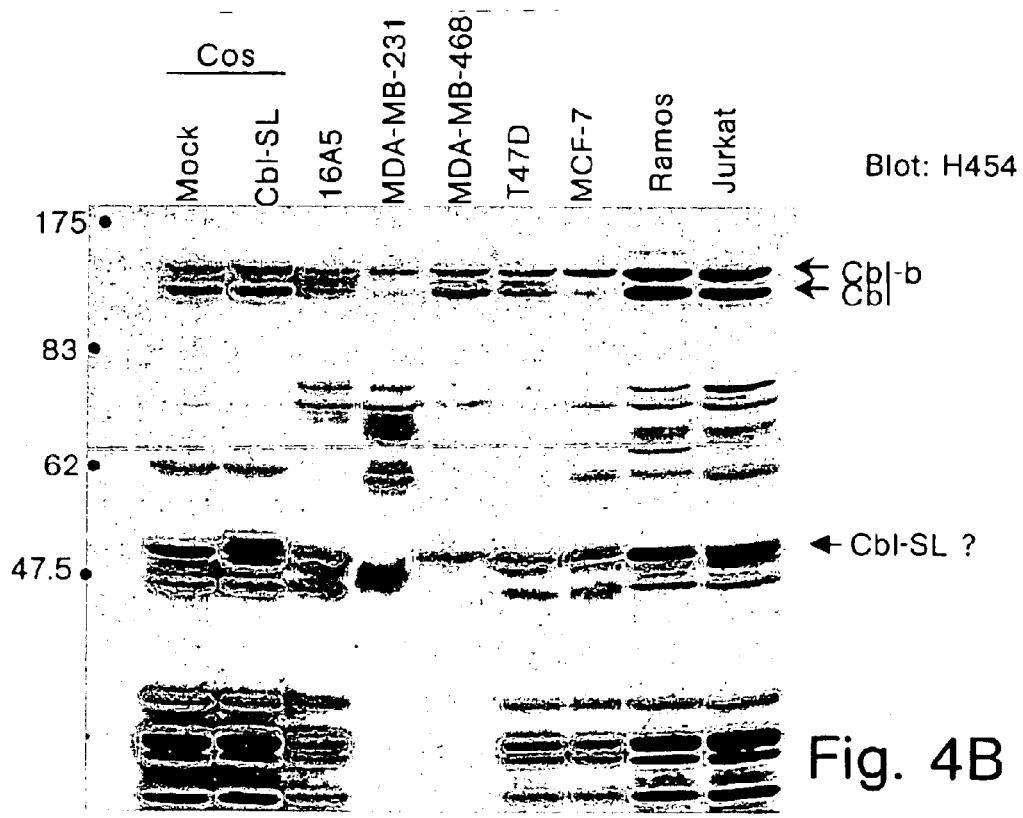
FIG. 4B depicts the same blot used in FIG. 4A but incubated with an anti-cbl-b specific antibody.

Different cell lines were lysed and 50 µg lysate samples were loaded on a 7.5% SDS-PAGE gel. The membrane was blotted with the anti-Cbl-SL#2 serum. As indicated in FIG. 4A, a band detected at about 50 kDa co-migrates with the transfected Cbl-SL and corresponds to the endogenous Cbl-SL. The same membrane was stripped and reblotted with the H454 antibody (anti-Cbl-b from Santa Cruz) which reacts with Cbl, Cbl-b and Cbl-SL. The results are depicted in FIG. 4B.

Example 4

Epidermal Growth Factor (EGF)-Induced Association of Cbl-SL with the EGF Receptor (EGF-R) and Grb2

Figure 5A:
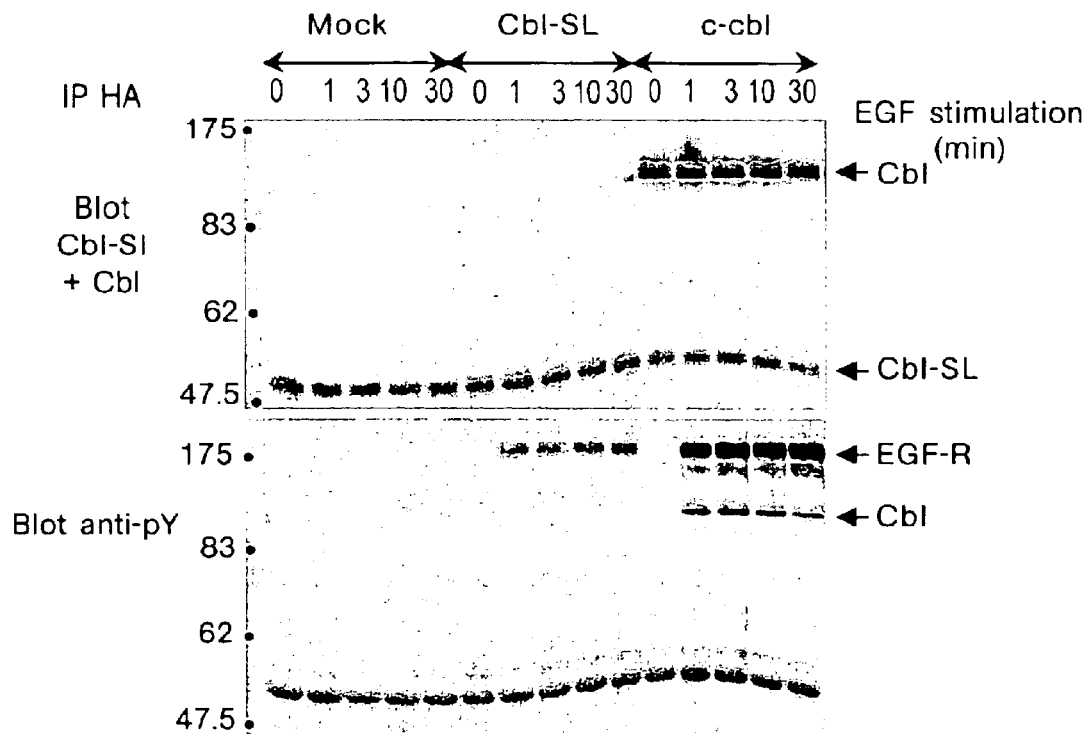
FIG. 5A shows an Epidermal Growth Factor (EGF)-induced association of cbl-SL with the EGF Receptor (EGF-R) and Grb2 using a western blot.
Figure 5B:
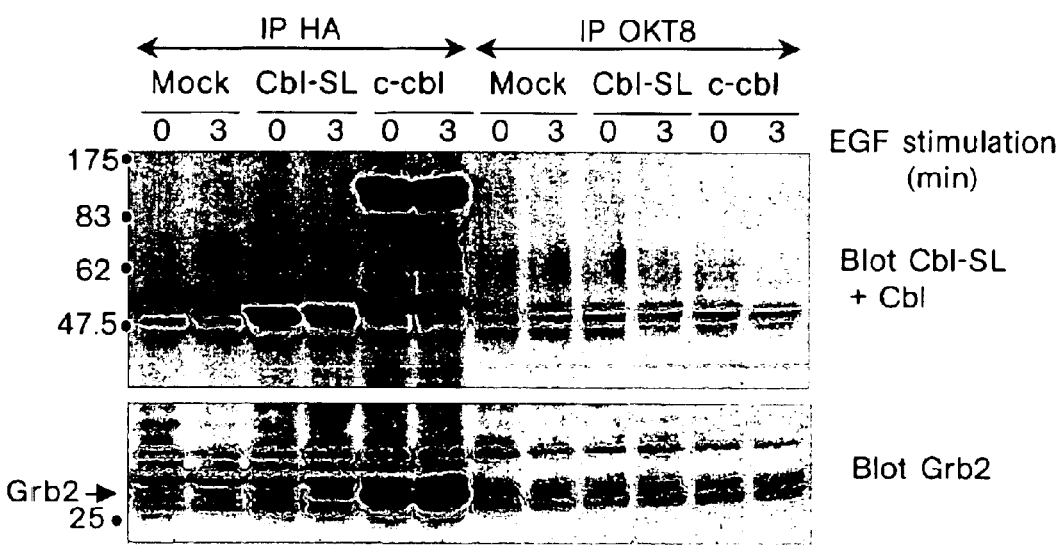
FIG. 5B shows that an association between Cbl-SL and Grb-2 was detected after EGF stimulation, in comparison to Cbl-Grb-2 association which is detectable both before and after EGF stimulation.

Cos 7 cells were transfected with pcDNA3 (mock), Cbl-SL or Cbl. After 48h, cells were starved for 5 hours in DMEM medium supplemented with 0.5% FCS, and then stimulated for the indicated times with EGF (100 ng/ml). Cells were then lysed with 1 ml lysis buffer. 200 µg protein samples were immunoprecipitated with anti-HA antibody. After transfer of the gel, the membrane was blotted with a mixture of anti-Cbl-SL+Cbl (FIG. 5A, upper blot); after stripping, the membrane was reblotted with antipY (FIG. 5A, lower blot). Tyrosine phosphorylation of Cbl-SL was not detected in this experiment. However, an associated tyrosine phosphorylated band corresponding to the EGF-R is observed in anti-Cbl-SL immunoprecipitates from lysates of EGF-stimulated cells. In a separate experiment, 400 µg of proteins isolated earlier (preceding paragraph), were immunoprecipitated with anti-HA or OKT8 (isotype-matched control) antibody. Immunoprecipitates were separated on a 12% SDS-PAGE gel. After transfer, the membrane was cut in two parts: the upper part was blotted with a mixture of anti-Cbl-SL#2 and anti-Cbl to visualize transfected Cbl-SL and Cbl (as shown in FIG. 5B); the lower part (FIG. 5B) was blotted with an anti-Grb-2 antibody (Santa Cruz). In this experiment, association between Cbl-SL and Grb-2 was detected after EGF stimulation, whereas Cbl-Grb-2 association is detectable both before and after EGF stimulation.

Example 5

In Vitro Binding of Cbl-SL with GST-Fusion Proteins of Signaling Proteins

Figure 6:
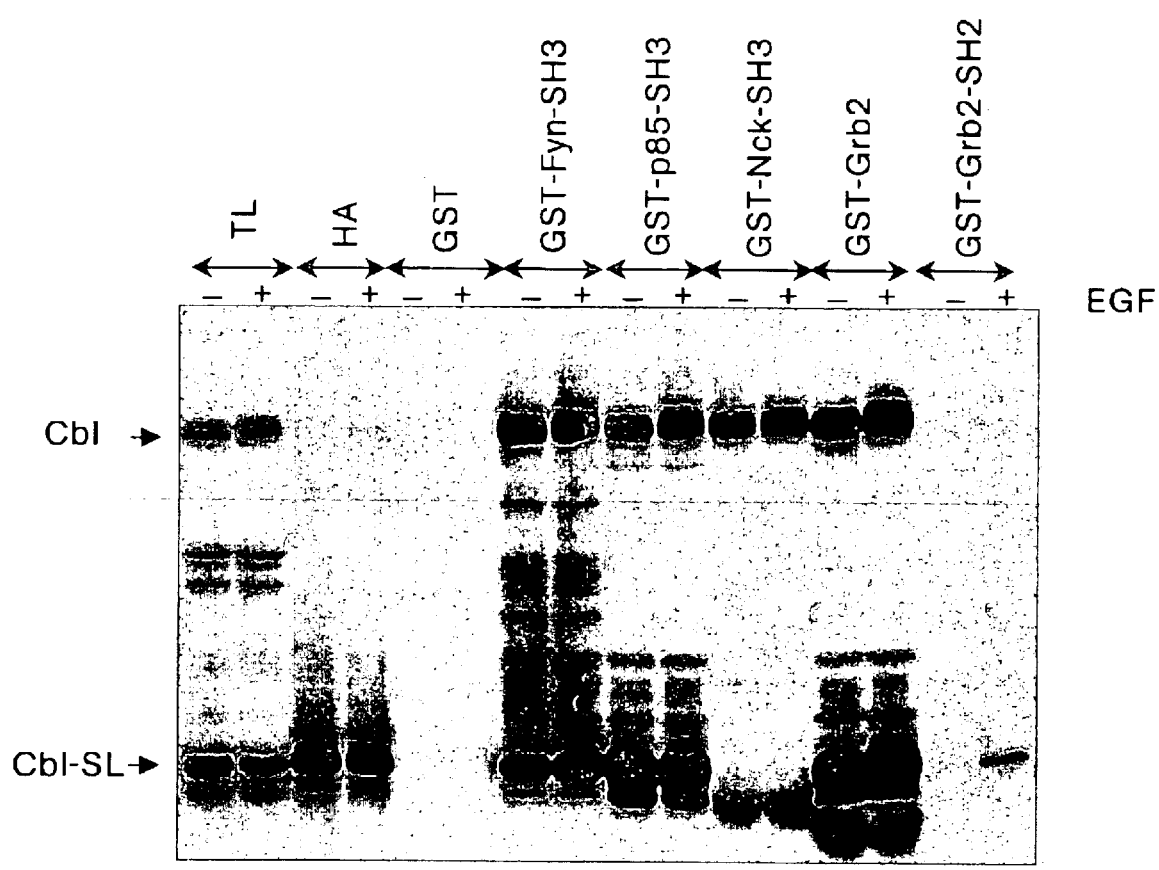
FIG. 6 depicts the in vitro association of cbl-SL binds with the SH3 domains of Fyn, p85, Nck, as well as with Grb-2, in the presence or absence of EGF stimulation.

Cos 7 cells were transfected with Cbl-SL; after 48h, cells were starved for 5 hours and then stimulated (+) or not (-) with EGF (100 ng/ml) for 5 minutes. 800 µg of proteins were mixed for 4 hours with 20 µg of different GST-fusion proteins indicated on top of the blot in FIG. 6. Precipitates were loaded on a 8% gel. After transfer, the membrane was blotted with a mixture of anti-Cbl-SL#2 and anti-Cbl antibodies. As shown in FIG. 6, Cbl-SL binds in vitro with the SH3 domains of Fyn and p85, as well as with Grb-2. A very small amount of Cbl-SL was found to bind to the SH2 domain of Grb-2, only after EGF stimulation. In contrast to Cbl, Cbl-SL did not bind to a GST construct incorporating two N-terminal SH3 domains of Nck (GST-Nck-SH3).

Example 6

Overexpression of Cbl-SL Facilitates the Downregulation of the EGFR Upon EGF Stimulation In view of the ability of Cbl-SL to physically interact with EGFR following EGF stimulation in transfected COS-7 cells (see the foregoing examples), we wished to assess if Cbl-SL may play a functional role in EGF signaling pathway. For this purpose, we used a co-transfection system in 293 HEK cells. As 293 HEK cells barely express the EGFR, we co-transfected these cells with an EGFR expression plasmid together with the vector alone, HA-Cbl or HA-Cbl-SL expression plamids. After 36 hours, cells were serum-starved for 5 hours and stimulated by adding purified murine EGF (100 ng/ml) for the indicated times (FIG. 8). The whole cell lysates were then analyzed by anti-Tyr(P) and anti-EGFR immunoblotting.

Overexpression of HA-Cbl (FIG. 8, top panel, lanes 11–15) led to a more rapid decrease in the tyrosine phosphorylation signal on the 175 kDa band corresponding to the EGFR when compared to mock transfectants (lanes 1–5). Concomitantly, a faster decrease in the EGFR protein level was observed (FIG. 8, middle panel). Notably, overexpression of HA-Cbl-SL (lanes 6–10) led to effects comparable to that of HA-Cbl overexpression. For example, significantly lower EGFR protein and phosphotyrosine signals were observed at 20 and 30 minutes after EGF stimulation compared to those in mock transfected cells. Overall, these results indicate that Cbl-SL is capable of negatively regulating the EGFR.

TABLE I

| Sequences with partial homologies to cbl-SL |
|---|
| Sequences with GenBank and EMBL (*) accession numbers: AA113289, AA112513, F22931*, X89223, X57110, U26710. |

Equivalents

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety. What is claimed is presented below and is followed by a Sequence Listing.

What is claimed is:

1. An isolated nucleic acid molecule selected from the group consisting of:
   (a) a nucleic acid molecule consisting of the nucleic acid of SEQ ID NO: 3
   (b) nucleic acid molecules that differ from the nucleic acid molecules of (a) in codon sequence due to the degeneracy of the genetic code, and
   (c) nucleic acid molecules fully complementary to SEQ ID NO:1 or SEQ ID NO:3.

2. The isolated nucleic acid molecule of claim 1, wherein the isolated nucleic acid molecule comprises SEQ ID NO:1.

3. The isolated nucleic acid molecule of claim 1, wherein the isolated nucleic acid molecule is the nucleic acid molecule of SEQ ID NO:3.

4. An expression vector comprising the isolated nucleic acid molecule of claim 1 operably linked to a promoter.

5. A host cell transformed or transfected with the expression vector of claim 4.

6. A composition comprising:
   an isolated nucleic acid molecule of claim 1 and a pharmaceutically acceptable carrier.

* * * * *

UNITED STATES PATENT AND TRADEMARK OFFICE
CERTIFICATE OF CORRECTION

PATENT NO.    : 6,867,292 B1
DATED         : March 15, 2005
INVENTOR(S)   : Hamid Band and Francescopaolo Borriello It is certified that error appears in the above-identified patent and that said Letters Patent is hereby corrected as shown below:

Column 55,
Line 52, after "of" insert -- SEQ ID NO: 1 or --.

Signed and Sealed this

Twenty-eighth Day of June, 2005

JON W. DUDAS
*Director of the United States Patent and Trademark Office*

SEQUENCE LISTING

<160> NUMBER OF SEQ ID NOS: 10

<210> SEQ ID NO 1
<211> LENGTH: 1547
<212> TYPE: DNA
<213> ORGANISM: Homo Sapiens
<220> FEATURE:
<221> NAME/KEY: CDS
<222> LOCATION: (13)...(1434)

<400> SEQUENCE: 1
cgcgaggctc cc atg gct ctg gcg gtg gcc ccg tgg ggg cga cag tgg gaa    51

-continued

```
                Met Ala Leu Ala Val Ala Pro Trp Gly Arg Gln Trp Glu
                 1               5                   10 gag gcc cgc gcc ctg ggc cgg gca gtc agg atg ctg cag cgc cta gaa      99
Glu Ala Arg Ala Leu Gly Arg Ala Val Arg Met Leu Gln Arg Leu Glu
     15                  20                  25 gag caa tgc gtc gac ccc cgg ctg tcc gtg agt ccc cct tcg ctg cgg     147
Glu Gln Cys Val Asp Pro Arg Leu Ser Val Ser Pro Pro Ser Leu Arg
 30                  35                  40                  45 gac ctg ctg ccc cgc aca gcg cag ctg ctt cga gag gtg gcc cat tct     195
Asp Leu Leu Pro Arg Thr Ala Gln Leu Leu Arg Glu Val Ala His Ser
             50                  55                  60 cgg cgg gcg gcc ggc gga ggc ggc ccc ggg ggt ccc ggc ggc tct ggg     243
Arg Arg Ala Ala Gly Gly Gly Gly Pro Gly Gly Pro Gly Gly Ser Gly
         65                  70                  75 gac ttt cta ctc atc tac ctg gcc aat ctg gag gcc aag agc agg cag     291
Asp Phe Leu Leu Ile Tyr Leu Ala Asn Leu Glu Ala Lys Ser Arg Gln
             80                  85                  90 gtg gcc gcg ctg ctg cct ccc cgg ggc cga agg agt gcc aac gac gag     339
Val Ala Ala Leu Leu Pro Pro Arg Gly Arg Arg Ser Ala Asn Asp Glu
         95                 100                 105 ctc ttc cgg gcg ggc tcc aga ctc agg cga cag ctg gcc aag ctg gcc     387
Leu Phe Arg Ala Gly Ser Arg Leu Arg Arg Gln Leu Ala Lys Leu Ala
110                 115                 120                 125 atc atc ttc agc cac atg cac gca gag ctg cac gca ctc ttc ccc ggg     435
Ile Ile Phe Ser His Met His Ala Glu Leu His Ala Leu Phe Pro Gly
                130                 135                 140 gca aag tac tgt gga cac atg tac cag ctc acc aag gcc ccc gcc cac     483
Ala Lys Tyr Cys Gly His Met Tyr Gln Leu Thr Lys Ala Pro Ala His
            145                 150                 155 acc ttc tgg agg gaa agt tgc gga gcc cgg tgt gtg ctg ccc tgg gct     531
Thr Phe Trp Arg Glu Ser Cys Gly Ala Arg Cys Val Leu Pro Trp Ala
            160                 165                 170 gag ttt gag tcc ctc ctg ggc acc tgc cac cct gtg gaa cca ggc tgc     579
Glu Phe Glu Ser Leu Leu Gly Thr Cys His Pro Val Glu Pro Gly Cys
        175                 180                 185 aca gcc ctg gcc ttg cgc acc acc att gac ctc acc tgc agc ggg cac     627
Thr Ala Leu Ala Leu Arg Thr Thr Ile Asp Leu Thr Cys Ser Gly His
190                 195                 200                 205 gtg tcc atc ttc gag ttc gac gtc ttc acc agg ctc ttt cag cca tgg     675
Val Ser Ile Phe Glu Phe Asp Val Phe Thr Arg Leu Phe Gln Pro Trp
                210                 215                 220 cca aca ctc ctc aag aac tgg cag ctc ctg gca gtc aac cac cca ggc     723
Pro Thr Leu Leu Lys Asn Trp Gln Leu Leu Ala Val Asn His Pro Gly
            225                 230                 235 tac atg gcc ttc ctc acc tat gat gag gtc caa gag cgt ctg cag gcc     771
Tyr Met Ala Phe Leu Thr Tyr Asp Glu Val Gln Glu Arg Leu Gln Ala
            240                 245                 250 tgc agg gac aag cca ggc agt tac atc ttc cgg ccc agc tgt act cgc     819
Cys Arg Asp Lys Pro Gly Ser Tyr Ile Phe Arg Pro Ser Cys Thr Arg
        255                 260                 265 ctg ggg cag tgg gcc atc ggc tat gtg agc tca gat ggc agc atc ctg     867
Leu Gly Gln Trp Ala Ile Gly Tyr Val Ser Ser Asp Gly Ser Ile Leu
270                 275                 280                 285 cag acc atc cct gcc aac aaa ccc ctg tcc cag gtg ctc ctg gag gga     915
Gln Thr Ile Pro Ala Asn Lys Pro Leu Ser Gln Val Leu Leu Glu Gly
                290                 295                 300 cag aag gac ggc ttc tac ctc tac cca gat gga aag acc cac aac cca     963
Gln Lys Asp Gly Phe Tyr Leu Tyr Pro Asp Gly Lys Thr His Asn Pro
            305                 310                 315 gac ctg act gag ctc ggc cag gca gaa ccc cag cag cgc atc cac gtg    1011
```

```
Asp Leu Thr Glu Leu Gly Gln Ala Glu Pro Gln Gln Arg Ile His Val
        320                 325                 330 tca gag gag cag ctg cag ctc tac tgg gcc atg gac tca aca ttt gag    1059
Ser Glu Glu Gln Leu Gln Leu Tyr Trp Ala Met Asp Ser Thr Phe Glu
    335                 340                 345 ctc tgc aag atc tgt gct gag agc aac aag gat gtg aag att gag ccg    1107
Leu Cys Lys Ile Cys Ala Glu Ser Asn Lys Asp Val Lys Ile Glu Pro
350                 355                 360                 365 tgc ggg cac ctg ctc tgc agc tgc tgc ctg gct gcc tgg cag cac tcg    1155
Cys Gly His Leu Leu Cys Ser Cys Cys Leu Ala Ala Trp Gln His Ser
                370                 375                 380 gac agc cag acc tgc ccc ttc tgc cgc tgc gag atc aag ggc tgg gag    1203
Asp Ser Gln Thr Cys Pro Phe Cys Arg Cys Glu Ile Lys Gly Trp Glu
        385                 390                 395 gcc gtg agt atc tac cag ttc cac ggt cag gct act gct gag gac tca    1251
Ala Val Ser Ile Tyr Gln Phe His Gly Gln Ala Thr Ala Glu Asp Ser
    400                 405                 410 ggg aac agc agt gac cag gaa ggc agg gag ttg gag ctg ggg cag gtg    1299
Gly Asn Ser Ser Asp Gln Glu Gly Arg Glu Leu Glu Leu Gly Gln Val
415                 420                 425 ccc ctt tcg gct cct cca ttg ccc cca cgg cca gat ctg ccc ccc agg    1347
Pro Leu Ser Ala Pro Pro Leu Pro Pro Arg Pro Asp Leu Pro Pro Arg
430                 435                 440                 445 aag ccc aga aat gcc cag ccg aaa gtg aga ctc cta aag ggg aac tcc    1395
Lys Pro Arg Asn Ala Gln Pro Lys Val Arg Leu Leu Lys Gly Asn Ser
                450                 455                 460 cct cca gct gcg ctg gga ccc cag gac cct gcc ccg gcc tgaaggccag    1444
Pro Pro Ala Ala Leu Gly Pro Gln Asp Pro Ala Pro Ala
                465                 470 ggcacccaga tgtgctgctc aagggagccc caagggctgg aagggggttg tgaaaccgaa   1504
ataaactgcc aagcctggtc tgtcaaaaaa aaaaaaaaaa aaa                     1547

<210> SEQ ID NO 2
<211> LENGTH: 474
<212> TYPE: PRT
<213> ORGANISM: Homo Sapiens

<400> SEQUENCE: 2

Met Ala Leu Ala Val Ala Pro Trp Gly Arg Gln Trp Glu Glu Ala Arg
1               5                   10                  15

Ala Leu Gly Arg Ala Val Arg Met Leu Gln Arg Leu Glu Glu Gln Cys
            20                  25                  30

Val Asp Pro Arg Leu Ser Val Ser Pro Pro Ser Leu Arg Asp Leu Leu
        35                  40                  45

Pro Arg Thr Ala Gln Leu Leu Arg Glu Val Ala His Ser Arg Arg Ala
    50                  55                  60

Ala Gly Gly Gly Pro Gly Gly Pro Gly Gly Ser Gly Asp Phe Leu
65              70                  75                  80

Leu Ile Tyr Leu Ala Asn Leu Glu Ala Lys Ser Arg Gln Val Ala Ala
                85                  90                  95

Leu Leu Pro Pro Arg Gly Arg Arg Ser Ala Asn Asp Glu Leu Phe Arg
            100                 105                 110

Ala Gly Ser Arg Leu Arg Arg Gln Leu Ala Lys Leu Ala Ile Ile Phe
        115                 120                 125

Ser His Met His Ala Glu Leu His Ala Leu Phe Pro Gly Ala Lys Tyr
    130                 135                 140

Cys Gly His Met Tyr Gln Leu Thr Lys Ala Pro Ala His Thr Phe Trp
```

-continued

```
            145                 150                 155                 160
    Arg Glu Ser Cys Gly Ala Arg Cys Val Leu Pro Trp Ala Glu Phe Glu
                    165                 170                 175
    Ser Leu Leu Gly Thr Cys His Pro Val Glu Pro Gly Cys Thr Ala Leu
                    180                 185                 190
    Ala Leu Arg Thr Thr Ile Asp Leu Thr Cys Ser Gly His Val Ser Ile
                    195                 200                 205
    Phe Glu Phe Asp Val Phe Thr Arg Leu Phe Gln Pro Trp Pro Thr Leu
                    210                 215                 220
    Leu Lys Asn Trp Gln Leu Leu Ala Val Asn His Pro Gly Tyr Met Ala
    225                 230                 235                 240
    Phe Leu Thr Tyr Asp Glu Val Gln Glu Arg Leu Gln Ala Cys Arg Asp
                    245                 250                 255
    Lys Pro Gly Ser Tyr Ile Phe Arg Pro Ser Cys Thr Arg Leu Gly Gln
                    260                 265                 270
    Trp Ala Ile Gly Tyr Val Ser Ser Asp Gly Ser Ile Leu Gln Thr Ile
                    275                 280                 285
    Pro Ala Asn Lys Pro Leu Ser Gln Val Leu Leu Glu Gly Gln Lys Asp
                    290                 295                 300
    Gly Phe Tyr Leu Tyr Pro Asp Gly Lys Thr His Asn Pro Asp Leu Thr
    305                 310                 315                 320
    Glu Leu Gly Gln Ala Glu Pro Gln Gln Arg Ile His Val Ser Glu Glu
                    325                 330                 335
    Gln Leu Gln Leu Tyr Trp Ala Met Asp Ser Thr Phe Glu Leu Cys Lys
                    340                 345                 350
    Ile Cys Ala Glu Ser Asn Lys Asp Val Lys Ile Glu Pro Cys Gly His
                    355                 360                 365
    Leu Leu Cys Ser Cys Cys Leu Ala Ala Trp Gln His Ser Asp Ser Gln
                    370                 375                 380
    Thr Cys Pro Phe Cys Arg Cys Glu Ile Lys Gly Trp Glu Ala Val Ser
    385                 390                 395                 400
    Ile Tyr Gln Phe His Gly Gln Ala Thr Ala Glu Asp Ser Gly Asn Ser
                    405                 410                 415
    Ser Asp Gln Glu Gly Arg Glu Leu Glu Leu Gly Gln Val Pro Leu Ser
                    420                 425                 430
    Ala Pro Pro Leu Pro Pro Arg Pro Asp Leu Pro Pro Arg Lys Pro Arg
                    435                 440                 445
    Asn Ala Gln Pro Lys Val Arg Leu Leu Lys Gly Asn Ser Pro Pro Ala
                    450                 455                 460
    Ala Leu Gly Pro Gln Asp Pro Ala Pro Ala
    465                 470

<210> SEQ ID NO 3
<211> LENGTH: 1422
<212> TYPE: DNA
<213> ORGANISM: Homo Sapiens

<400> SEQUENCE: 3
atggctctgg cggtggcccc gtgggggcga cagtgggaag aggcccgcgc cctgggccgg      60
gcagtcagga tgctgcagcg cctagaagag caatgcgtcg accccggct gtccgtgagt     120 ccccttcgc tgcgggacct gctgccccgc acagcgcagc tgcttcgaga ggtggcccat     180
tctcggcggg cggccggcgg aggcggcccc gggggtcccg gcggctctgg ggactttcta     240
ctcatctacc tggccaatct ggaggccaag agcaggcagg tggccgcgct gctgcctccc     300
```

-continued

```
cggggccgaa ggagtgccaa cgacgagctc ttccgggcgg gctccagact caggcgacag    360
ctggccaagc tggccatcat cttcagccac atgcacgcag agctgcacgc actcttcccc    420
ggggcaaagt actgtggaca catgtaccag ctcaccaagg cccccgccca cccttctgg     480 agggaaagtt gcggagcccg tgtgtgctg ccctgggctg agtttgagtc cctcctgggc     540
acctgccacc ctgtggaacc aggctgcaca gccctggcct tgcgcaccac cattgacctc    600
acctgcagcg ggcacgtgtc catcttcgag ttcgacgtct tcaccaggct ctttcagcca    660
tggccaacac tcctcaagaa ctggcagctc tggcagtca accacccagg ctacatggcc     720
ttcctcacct atgatgaggt ccaagagcgt ctgcaggcct gcagggacaa gccaggcagt    780
tacatcttcc ggcccagctg tactcgcctg gggcagtggg ccatcggcta tgtgagctca    840
gatggcagca tcctgcagac catccctgcc aacaaacccc tgtcccaggt gctcctggag    900
ggacagaagg acggcttcta cctctaccca gatggaaaga cccacaaccc agacctgact    960
gagctcggcc aggcagaacc ccagcagcgc atccacgtgt cagaggagca gctgcagctc   1020
tactgggcca tggactccac atttgagctc tgcaagatct gtgctgagag caacaaggat   1080
gtgaagattg agccgtgcgg gcacctgctc tgcagctgct gcctggctgc ctggcagcac   1140
tcggacagcc agacctgccc cttctgccgc tgcgagatca agggctggga ggccgtgagt   1200
atctaccagt tccacggtca ggctactgct gaggactcag ggaacagcag tgaccaggaa   1260
ggcagggagt tggagctggg gcaggtgccc ctttcggctc ctccattgcc cccacggcca   1320
gatctgcccc ccaggaagcc cagaaatgcc cagccgaaag tgagactcct aaagggaac    1380 tccccctccag ctgcgctggg accccaggac cctgccccgg cc                     1422
```

<210> SEQ ID NO 4
<211> LENGTH: 462
<212> TYPE: DNA
<213> ORGANISM: Homo Sapiens
<220> FEATURE:
<221> NAME/KEY: unsure
<222> LOCATION: (100)...(100)
<223> OTHER INFORMATION: unknown
<221> NAME/KEY: unsure
<222> LOCATION: (103)...(103)
<223> OTHER INFORMATION: unknown
<221> NAME/KEY: unsure
<222> LOCATION: (105)...(105)
<223> OTHER INFORMATION: unknown
<221> NAME/KEY: unsure
<222> LOCATION: (125)...(125)
<223> OTHER INFORMATION: unknown
<221> NAME/KEY: unsure
<222> LOCATION: (128)...(128)
<223> OTHER INFORMATION: unknown
<221> NAME/KEY: unsure
<222> LOCATION: (130)...(130)
<223> OTHER INFORMATION: unknown
<221> NAME/KEY: unsure
<222> LOCATION: (220)...(220)
<223> OTHER INFORMATION: unknown
<221> NAME/KEY: unsure
<222> LOCATION: (389)...(389)
<223> OTHER INFORMATION: unknown
<221> NAME/KEY: unsure
<222> LOCATION: (409)...(409)
<223> OTHER INFORMATION: unknown

<400> SEQUENCE: 4

```
tgacagacca ggcttggcag tttatttcgg tttcacaacc cccttccagc ccttggggtc     60
ccttgagcag cacatctggg tgccctggcc ttcagcgggn agngngtcct ggggtcccag    120
```

```
cgcangangn gggagttccc ctttaggagt ctcactttcg gctgggcatt tctgggcttc      180 ctgggggca gatctggccg tgggggcaat ggaggagccn aaaggggcac ctgcccaggc      240
tccaactccc tgccttcctg gtcactgctg ttccctgagt cctcagcagt agcctgaccg      300
tagaactggt agatactcac ggcctcccag cccttgatct cgcagcggca gaaggggcag    360
gtctgggctg tccgagtgct gccaggcanc caggcagcag ctgcagaana ggtgcccgca    420
cggctcaatc ttcacatcct tgttgctctc agcacagatc tt                       462

<210> SEQ ID NO 5
<211> LENGTH: 435
<212> TYPE: DNA
<213> ORGANISM: Homo Sapiens
<220> FEATURE:
<221> NAME/KEY: unsure
<222> LOCATION: (51)...(51)
<223> OTHER INFORMATION: unknown
<221> NAME/KEY: unsure
<222> LOCATION: (65)...(65)
<223> OTHER INFORMATION: unknown

<400> SEQUENCE: 5
agggacaagc caggcagtta catcttccgg cccagctgta ctcgcctggg ncagtgggcc     60
atcgntattg tgagctcaga tggcagcatc ctgcagacca tccctgccaa caaacccctg   120
tcccaggtgc tcctggaggg acagaaggac ggcttctacc tctacccaga tggaaagacc   180
cacaacccag acctgactga gctcggccag gcagaacccc agcagcgcat ccacgtgtca   240
gaggagcagc tgcagctcta ctgggccatg gactccacat ttgagctctg caagatctgt   300
gctgagagca acaaggatgt gaagattgag ccgtgcgggc acctgctctg cagctgctgc   360
cttggcttgc cttggcagaa cttcggacag ccagaccttg ccccttcttg cccgctgcga   420
gattcaaggg cttgg                                                     435

<210> SEQ ID NO 6
<211> LENGTH: 491
<212> TYPE: DNA
<213> ORGANISM: Sus Scrofa
<220> FEATURE:
<221> NAME/KEY: unsure
<222> LOCATION: (320)...(320)
<223> OTHER INFORMATION: unknown
<221> NAME/KEY: unsure
<222> LOCATION: (373)...(373)
<223> OTHER INFORMATION: unknown
<221> NAME/KEY: unsure
<222> LOCATION: (377)...(377)
<223> OTHER INFORMATION: unknown
<221> NAME/KEY: unsure
<222> LOCATION: (392)...(392)
<223> OTHER INFORMATION: unknown
<221> NAME/KEY: unsure
<222> LOCATION: (397)...(397)
<223> OTHER INFORMATION: unknown
<221> NAME/KEY: unsure
<222> LOCATION: (420)...(420)
<223> OTHER INFORMATION: unknown
<221> NAME/KEY: unsure
<222> LOCATION: (423)...(423)
<223> OTHER INFORMATION: unknown
<221> NAME/KEY: unsure
<222> LOCATION: (427)...(427)
<223> OTHER INFORMATION: unknown
<221> NAME/KEY: unsure
<222> LOCATION: (431)...(431)
<223> OTHER INFORMATION: unknown

<400> SEQUENCE: 6
```

```
gtgagctcag atggcagcat cctgcagacc atccctctca acaaacctct gttccaagca    60
ctcctggaag gacaaaagga aggcttctac ctctaccctg atgggaagaa ccacaacccg   120
gacctgacgg agctctgcgt aacgggaccc tatcaacgca tccacgtgtc ggaggagcag   180
ctgcagctgt actgggccat gaactccaca tacgagctct gcaagatctg tgccgagaga   240
aacaaggacg tgaagattga gccatgcggg gcactgctct gcagcccgct gcctgggcta   300
cctggcagaa ctcagacagn ccagacctgc ccttttctgg ccgctgccag attcaagggg   360
ccagagcctg tgngttntcc atcagttttcc anggganggc cagagggaag ccgggcgctn   420
aangacncca nggggacagc agtggccaag ggaagatggg ggatgaggag ctgggccagg   480
tggaccccct c                                                        491

<210> SEQ ID NO 7
<211> LENGTH: 2230
<212> TYPE: DNA
<213> ORGANISM: C. Elegans

<400> SEQUENCE: 7
ctatgatcat tacatcctaa ttaattgcca ctggacttca catcatatca ccgtttcacc    60
gggaatgggt tcaataaaca caattttttca ccggatacat cggtttgtca atggcacagg   120
caataatgcg cgatttgttc ccagcacaaa caactcgacg gaagcgttga cactcagtcc   180
gagagctgtt cccagcacag tttcactatt cgaaatccca tcagcttcgg agatgcccgg   240
tttctgcagt gaagaggatc gtcgattttt gctcaaagca tgcaagttta tggatcaagt   300
agtgaagagt tgtcatagcc caagactgaa tttgaaaaat cgccgccctt tcattttgga   360
cattctacct gatacttata cgcatttaat gctgatattc acacaaaaca atgcatact    420 ccaagacaac gactacttga aaatctttct ggagagtatg atcaacaagt gcaaagagat   480
catcaaactg ttcaagacgt cagctatcta caatgaccag tctgaagaac gacggaagct   540
tacgaaaatg tcactaacat tttcacatat gcttttcgag attaaagcat tatttccgga   600
aggtatctat attgaagacc ggtttcggat gacaaagaag gaagccgaaa gcttttggag   660
tcatcatttt acaaaaaaaa acattgtacc ctggtcaaca ttttttactg cattagaaaa   720
gcaccatgga tcaacgatag gaaaaatgga agcagccgaa ttaaaagcta cgatagactt   780
gagcggagat gattttattt cgaattttga gtttgatgtg tttacaaggt tattctaccc   840
tttcaaaaca ctgatcaaaa attggcaaac actcaccacc gcccatcccg gatactgtgc   900
atttctcaca tacgatgagg tcaaaaaacg gttagaaaaa ttaacgaaaa aacctggaag   960
ctacatcttc cggttatcat gcacacgtcc tggacaatgg gcaataggat acgtagctcc  1020
ggatggaaag atttatcaga caataccaca gaataaaagt ttgattcaag cactacatga  1080 aggcccataaa gaaggatttt atatttaccc gaacggtaga gatcaagata ttaacttatc  1140
caaattgatg gatgtgccac aagcggacag agtgcaagtg accagtgaac aatacgagtt  1200
gtattgtgag atgggcacaa cattcgagtt gtgcaaaatt tgtgacgata acgagaagaa  1260
catcaaaatt gagccatgtg gacatttgct ctgcgcaaaa tgtttggcta actggcagga  1320
ttcggatggt ggtggcaaca catgtccatt ctgccgctac gaaatcaaag gaacaaatcg  1380
tgtgattatt gacaggttca gcccactccc ggtagaaatt gaaaaagcga aaatgtagc   1440 tgctgcggag aagaagctga tctcattagt tcccgacgtg cctcccagaa cgtatgtgtc  1500
ccaatgttct caaagtttgc tgcatgacgc gtcaaactca attccgtcgg tcgacgagtt  1560
gccgttggtg ccgccaccgt tgccaccgaa agcattgggt accctggaca ctttgaattc  1620
```

-continued

```
gtcacaaaca tcctcttcat acgtgaacat caaagagctg gaaaatgttg aaacaagcgg   1680
agaagcattg gcacaagtgg taaaccggca acgggcgcct tcaatccaag ctccaccact   1740
accgccaagg ttatcagcga gcgagcacca accacaccac ccatacacaa atacgaacag   1800
tgagcgggag tagacttgtg taaatgttca tcttaccgct ttatactgca attttcattc   1860
ccccacttat catagaacta ttcttccaca acaacatatt gccgtgacta gaactggtaa   1920
cactacatca ttctttgtta aaacgttatt atatctctat ttcttttttcg cctactcctt   1980
tccgtttttt tttcaaattt tgtcaatttt cctacagcgt tctgactcct attggtaagc   2040
aatcatgtca tatcttgtta aattttcatg ttaatttctt actctcgctg tcccagattt   2100
tacgagtttt tcaggaaacg tttgattttg ttctattcta caatttccat cgcccccaac   2160
ctgtcgtgta ttttctatgt gtcactctga agaaaacaag tttagacttt ttaaaaaaaa   2220
aaaaaaaaaa                                                          2230

<210> SEQ ID NO 8
<211> LENGTH: 3090
<212> TYPE: DNA
<213> ORGANISM: Homo Sapiens

<400> SEQUENCE: 8
gaattccggg cccggatagc cggcggcggc ggcggcggcg gcggcggcgg cggccgggag     60
aggcccctcc ttcacgccct gcttctctcc ctcgctcgca gtcgagccga gccggcggac    120
ccgcctgggc tccgaccctg cccaggccat ggccggcaac gtgaagaaga gctctggggc    180
cgggggcggc acgggctccg ggggctcggg ttcggtggc ctgattgggc tcatgaagga    240
cgccttccag ccgcaccacc accaccacca ccacctcagc ccccacccgc cggggacggt    300
ggacaagaag atggtggaga gtgctggaga gctcatggac aaggtggtgc ggttgtgtca    360
gaacccaaag ctggcgctaa agaatagccc accttatatc ttagacctgc taccagatac    420
ctaccagcat ctccgtacta tcttgtcaag atatgagggg aagatggaga cacttggaga    480
aaatgagtat tttagggtgt ttatggagaa tttgatgaag aaaactaagc aaaccataag    540
cctcttcaag gagggaaaag aaagaatgta tgaggagaat tctcagccta ggcgaaacct    600
aaccaaactg tccctcatct tcagccacat gctggcagaa ctaaaaggaa tctttccaag    660
tggactcttt caggagaca catttcggat tactaaagca gatgctgcgg aattttggag    720
aaaagctttt ggggaaaaga caatagtccc ttggaagagc tttcgacagg ctctacatga    780
agtgcatccc atcagttctg ggctggaggc catggctctg aaatccacta ttgatctgac    840
ctgcaatgat tatatttcgg ttttttgaatt tgacatcttt acccgactct ttcagccctg    900
gtcctctttg ctcaggaatt ggaacagcct tgctgtaact catcctggct acatggcttt    960
tttgacgtat gacgaagtga aagctcggct ccagaaattc attcacaaac ctggcagtta   1020
tatcttccgg ctgagctgta ctcgtctggg tcagtgggct attgggtatg ttactgctga   1080
tgggaacatt ctccagacaa tccctcacaa taaacctctc ttccaagcac tgattgatgg   1140
cttcagggaa ggcttctatt tgtttcctga tggacgaaat cagaatcctg atctgactgg   1200
cttatgtgaa ccaactcccc aagaccatat caaagtgacc caggaacaat atgaattata   1260
ctgtgagatg ggctccacat tccaactatg taaaatatgt gctgaaaatg ataaggatgt   1320
aaagattgag ccctgtggac acctcatgtg cacatcctgt cttacatcct ggcaggaatc   1380
agaaggtcag ggctgtccctt tctgccgatg tgaaattaaa ggtactgaac ccatcgtggt   1440
```

-continued

```
agatccgttt gatcctagag ggagtggcag cctgttgagg caaggagcag agggagctcc      1500
ctccccaaat tatgatgatg atgatgatga acgagctgat gatactctct tcatgatgaa      1560
ggaattggct ggtgccaagg tggaacggcc gccttctcca ttctccatgg ccccacaagc      1620
ttcccttccc ccggtgccac cacgacttga ccttctgccg cagcgagtat gtgttccctc      1680
aagtgcttct gctcttggaa ctgcttctaa ggctgcttct ggctcccttc ataaagacaa      1740
accattgcca gtacctccca cacttcgaga tcttccacca ccaccgcctc cagaccggcc      1800
atattctgtt ggagcagaat cccgacctca agacgcccc ttgccttgta caccaggcga      1860
ctgtccctcc agagacaaac tgccccctgt ccccctctagc cgccttggag actcatggct      1920
gccccggcca atccccaaag taccagtatc tgccccaagt tccagtgatc cctggacagg      1980
aagagaatta accaaccggc actcacttcc attttcattg ccctcacaaa tggagcccag      2040
accagatgtg cctaggctcg gaagcacgtt cagtctggat acctccatga gtatgaatag      2100
cagcccatta gtaggtccag agtgtgacca ccccaaaatc aaaccttcct catctgccaa      2160
tgccatttat tctctggctg ccagacctct tcctgtgcca aaactgccac ctggggagca      2220
atgtgagggt gaagaggaca cagagtacat gactccctct tccaggcctc tacggccttt      2280
ggatacatcc cagagttcac gagcatgtga ttgcgaccag cagattgata gctgtacgta      2340
tgaagcaatg tataatattc agtcccaggc gccatctatc accgagagca gcacctttgg      2400
tgaagggaat ttggccgcag cccatgccaa cactggtccc gaggagtcag aaaatgagga      2460
tgatgggtat gatgtcccaa agccaccctgt gccggccgtg ctggcccgcc gaactctctc      2520
agatatctct aatgccagct cctcctttgg ctggttgtct ctggatggtg atcctacaac      2580
aaatgtcact gaaggtttcc aagttcccga gaggcctcca aaaccattcc cgcggagaat      2640
caactctgaa cggaaagctg gcagctgtca gcaaggtagt ggtcctgccg cctctgctgc      2700
caccgcctca cctcagctct ccagtgagat cgagaacctc atgagtcagg gtactcccta      2760
ccaggacatc cagaaagctt tggtcattgc ccagaacaac atcgagatgg ccaaaaacat      2820
cctccgggaa tttgtttcca tttcttctcc tgcccatgta gctacctagc acaccatctc      2880
cctgctgcag gtttagagga ccagtgagtt gggagttatt actcaagtgg cacctagaag      2940
ggcaggagtt cctttggtga cttcacagtg aagtcttgcc ctctctgtgg gatatcacat      3000
cagtggttcc aagatttcaa agtggtgaaa tgaaaatgga gcagctagta tgttttatta      3060
ttttatgggt cttgagtgca tttgaaggtg                                      3090
```

<210> SEQ ID NO 9
<211> LENGTH: 3982
<212> TYPE: DNA
<213> ORGANISM: Homo Sapiens

<400> SEQUENCE: 9

```
ctgggtcctg tgtgtgccac agggtgtgggg tgtccagcga gcggtctcct cctcctgcta       60
gtgctgctgc ggcgtcccgc ggcctccccg agtcgggcgg gaggggagag cgggtgtgga      120
tttgtcttga cggtaattgt tgcgtttcca cgtctcggag gcctgcgcgc tgggttgctc      180
cttcttcggg agcgagctgt tctcagcgat cccactccca gccggggctc cccacacaca      240
ctgggctgcg tgcgtgtgga gtgggacccg cgcacgcgcg tgtctctgga cagctacggc      300
gccgaaagaa ctaaaattcc agatggcaaa ctcaatgaat ggcagaaacc ctggtggtcg      360
aggaggaaat ccccgaaaag gtcgaatttt gggtattatt gatgctattc aggatgcagt      420 tggacccccct aagcaagctg ccgcagatcg caggaccgtg gagaagactt ggaagctcat      480
```

```
ggacaaagtg gtaagactgt gccaaaatcc caaacttcag ttgaaaaata gcccaccata    540
tatacttgat attttgcctg atacatatca gcatttacga cttatattga gtaaatatga    600
tgacaaccag aaacttgccc aactcagtga gaatgagtac tttaaaatct acattgatag    660
ccttatgaaa aagtcaaaac gggcaataag actctttaaa gaaggcaagg agagaatgta    720
tgaagaacag tcacaggaca gacgaaatct cacaaaactg tcccttatct tcagtcacat    780
gctggcagaa atcaaagcaa tctttcccaa tggtcaattc cagggagata actttcgtat    840
cacaaaagca gatgctgctg aattctggag aaagtttttt ggagacaaaa ctatcgtacc    900
atggaaagta ttcagacagt gccttcatga ggtccaccag attagctcta gcctggaagc    960
aatggctcta aaatcaacaa ttgatttaac ttgcaatgat tacatttcag ttttgaatt    1020 tgatattttt accaggctgt ttcagccttg gggctctatt ttgcggaatt ggaatttctt    1080
agctgtgaca catccaggtt acatggcatt tctcacatat gatgaagtta agcacgact    1140 acagaaatat agcaccaaac ccggaagcta tattttccgg ttaagttgca ctcgattggg    1200
acagtgggcc attggctatg tgactgggga tgggaatatc ttacagacca tacctcataa    1260
caagccctta tttcaagccc tgattgatgg cagcagggaa ggattttatc tttatcctga    1320
tgggaggagt tataatcctg atttaactgg attatgtgaa cctacacctc atgaccatat    1380
aaaagttaca caggaacaat atgaattata ttgtgaaatg ggctccactt ttcagctctg    1440
taagatttgt gcagagaatg acaaagatgt caagattgag ccttgtgggc atttgatgtg    1500
cacctcttgc cttacggcat ggcaggagtc ggatggtcag ggctgccctt tctgtcgttg    1560
tgaaataaaa ggaactgagc ccataatcgt ggaccccttt gatccaagag atgaaggctc    1620
caggtgttgc agcatcattg acccctttgg catgccgatg ctagacttgg acgacgatga    1680
tgatcgtgag gagtccttga tgatgaatcg gttggcaaac gtccgaaagt gcactgacag    1740
gcagaactca ccagtcacat caccaggatc tctctcccct gcccagagaa gaaagccaca    1800
gcctgaccca ctccagatcc cacatctaag cctgccaccc gtgcctcctc gcctggatct    1860
aattcagaaa ggcatagtta gatctcccctg tggcagccca acaggttcac caaagtcttc    1920
tccttgcatg gtgagaaaac aagataaacc actcccagca ccacctcctc ccttaagaga    1980
tcctcctcca ccgccacctg aaagacctcc accaatccca ccagacaata gactgagtag    2040
acacatccat catgtggaaa gcgtgccttc cagagacccg ccaatgcctc ttgaagcatg    2100
gtgccctcgg gatgtgtttg ggactaatca gcttgtggga tgtcgactcc taggggaggg    2160
ctctccaaaa cctggaatca cagcgagttc aaatgtcaat ggaaggcaca gtagagtggg    2220
ctctgaccca gtgcttatgc ggaaacacag acgccatgat ttgcctttag aaggagctaa    2280
ggtcttttcc aatggtcacc ttggaagtga agaatatgat gttcctcccc ggctttctcc    2340
tcctcctcca gttaccaccc tcctccctag cataaagtgt actggtccgt tagcaaattc    2400 tcttcagag aaaacaagag acccagtaga ggaagatgat gatgaataca agattccttc    2460 atccaccct gttccctga attcacaacc atctcattgt cataatgtaa aacctcctgt    2520
tcggtcctgt gataatggtc actgtatgct gaatggaaca catggtccat cttcagagaa    2580
gaaatcaaac atccctgact taagcatata tttaaaggga gatgttttg attcagcctc    2640 tgatcccgtg ccattaccac ctgccaggcc tccaactcgg gacaatccaa agcatggttc    2700
ttcactcaac aggacgccct ctgattatga tcttctcatc cctccattag gtgaagatgc    2760 tttttgatgcc ctccctccat ctctcccacc tcccccacct cctgcaaggc atagtctcat    2820
```

```
tgaacattca aaacctcctg gctccagtag ccggccatcc tcaggacagg atcttttct    2880 tcttccttca gatcccttg ttgatctagc aagtggccaa gttcctttgc ctcctgctag    2940
aaggttacca ggtgaaaatg tcaaaactaa cagaacatca caggactatg atcagcttcc   3000
ttcatgttca gatggttcac aggcaccagc cagaccccct aaaccacgac cgcgcaggac   3060
tgcaccagaa attcaccaca gaaaccccca tgggcctgag gcggcattgg aaaatgtcga   3120
tgcaaaaatt gcaaaactca tgggagaggg ttatgccttt gaagaggtga agagagcctt   3180
agagatagcc cagaataatg tcgaagttgc ccggagcatc ctccgagaat ttgccttccc   3240
tcctccagta tccccacgtc taaatctata gcagccagaa ctgtagacac caaaatggaa   3300
agcaatcgat gtattccaag agtgtggaaa taaagagaac tgagatggaa ttcaagagag   3360
aagtgtctcc tcctcgtgta gcagcttgag aagaggcttg ggagtgcagc ttctcaaagg   3420
agaccgatgc ttgctcagga tgtcgacagc tgtggcttcc ttgttttgc tagccatatt   3480 tttaaatcag ggttgaactg acaaaaataa tttaaagacg tttacttccc ttgaactttg   3540
aacctgtgaa atgctttacc ttgtttacaa tttggcaaag ttgcagtttg ttcttgtttt   3600
tagtttagtt ttgttttggt gttttgatac ctgtactgtg ttcttcacag acccttgta    3660 gcgtggtcag gtctgctgta acatttccca ccaactctct tgctgtccac atcaacagct   3720
aaatcattta ttcatatgga tctctaccat ccccatgcct tgcccaggtc cagttccatt   3780
tctctcattc acaagatgct ttgaaggttc tgattttcaa ctgatcaaac taatgcaaaa   3840
aaaaaaagta tgtattcttc actactgagt ttcttctttg gaaaccatca ctattgagag   3900
atgggaaaaa cctgaatgta taaagcattt atttgtcaat aaactgcctt ttgtaagggg   3960
ttttcacata aaaaaaaaaa aa                                             3982
```

<210> SEQ ID NO 10
<211> LENGTH: 17
<212> TYPE: PRT
<213> ORGANISM: Homo Sapiens

<400> SEQUENCE: 10

```
Arg Lys Pro Arg Asn Ala Gln Pro Lys Val Arg Leu Leu Lys Gly Asn
 1               5                  10                  15

Ser
```